(12) United States Patent
Studdert et al.

(10) Patent No.: US 11,052,170 B2
(45) Date of Patent: Jul. 6, 2021

(54) TEMPORARY DRESSING FOR AN INTERNAL WOUND

(71) Applicant: QTF INNOVATION LLC, Wilmette, IL (US)

(72) Inventors: Andrew Studdert, Wilmette, IL (US); Michael R. Miller, Winnetka, IL (US)

(73) Assignee: QTF INNOVATION LLC, Wilmette, IL (US)

( * ) Notice: Subject to any disclaimer, the term of this patent is extended or adjusted under 35 U.S.C. 154(b) by 188 days.

(21) Appl. No.: 16/283,249

(22) Filed: Feb. 22, 2019

(65) Prior Publication Data

US 2019/0275194 A1    Sep. 12, 2019

Related U.S. Application Data

(60) Provisional application No. 62/639,078, filed on Mar. 6, 2018.

(51) Int. Cl.
*A61L 15/60* (2006.01)
*A61F 13/00* (2006.01)
(Continued)

(52) U.S. Cl.
CPC .............. *A61L 15/60* (2013.01); *A61B 17/24* (2013.01); *A61F 13/00021* (2013.01);
(Continued)

(58) Field of Classification Search
CPC ... A61L 15/60; A61L 15/425; A61B 17/0057; A61B 2017/00632; A61B 2017/00991; A61B 17/12159; A61B 2017/00898; A61B 2017/12004; A61B 17/1204; A61B 17/132; A61B 17/12031; A61B 17/12036; A61B 17/12109; A61B 17/12113;
(Continued)

(56) References Cited

U.S. PATENT DOCUMENTS

| 3,648,683 A | * | 3/1972 | Brodie ...................... A61F 6/22 128/843 |
| 2014/0074144 A1 | * | 3/2014 | Shrivastava ......... A61B 17/221 606/200 |

(Continued)

*Primary Examiner* — Katherine H Schwiker
*Assistant Examiner* — Raihan R Khandker
(74) *Attorney, Agent, or Firm* — Husch Blackwell LLP

(57) ABSTRACT

The invention relates to a device for treating blood flow in an internal wound, including a handling member connected to a series of successively narrower tubes, each tube including a liquid-expandable article. The tubes can be pivotably connected to each other, allowing the tubes to conform to the contours of the wound, or fixed together. The tubes can be encased in a liquid-soluble layer that keeps the liquid-expandable article sequestered from liquids.

The stepwise-tapering profile of the device allows for its insertion into the internal wound with little or no resistance until fully seated. Upon encountering liquids within the wound, the liquid-soluble layer can dissolve to expose the liquid-expandable article. When exposed to the wound liquids, the liquid-expandable element can expand in volume, providing compressive pressure against internal wound surfaces and minimizing blood loss.

The tubes and the liquid-expandable element can include therapeutic agents for treating the wound.

10 Claims, 9 Drawing Sheets

(51) Int. Cl.
*A61B 17/24* (2006.01)
*A61F 13/12* (2006.01)
*A61B 17/12* (2006.01)
*A61L 15/42* (2006.01)
*A61B 17/132* (2006.01)
*A61B 17/00* (2006.01)

(52) U.S. Cl.
CPC .. *A61F 13/00063* (2013.01); *A61F 13/00068* (2013.01); *A61F 13/126* (2013.01); *A61B 17/0057* (2013.01); *A61B 17/1204* (2013.01); *A61B 17/12104* (2013.01); *A61B 17/12159* (2013.01); *A61B 17/12163* (2013.01); *A61B 17/132* (2013.01); *A61B 2017/00575* (2013.01); *A61B 2017/00601* (2013.01); *A61B 2017/00632* (2013.01); *A61B 2017/00654* (2013.01); *A61B 2017/00809* (2013.01); *A61B 2017/00849* (2013.01); *A61B 2017/00876* (2013.01); *A61B 2017/00893* (2013.01); *A61B 2017/00898* (2013.01); *A61B 2017/00942* (2013.01); *A61B 2017/00951* (2013.01); *A61B 2017/00991* (2013.01); *A61B 2017/12004* (2013.01); *A61F 2013/00476* (2013.01); *A61L 15/425* (2013.01); *A61M 2205/3344* (2013.01)

(58) Field of Classification Search
CPC . A61B 17/12122; A61B 17/12; A61B 17/159; A61B 17/12163; A61B 2017/00575; A61B 2017/00588; A61B 2017/00601; A61B 2017/00592; A61B 2017/00654; A61B 17/12181; A61B 17/12186; A61B 17/1219; A61B 17/12195; A61B 2017/4216; A61B 2017/4233; A61M 2205/3344; A61F 13/00021; A61F 6/22; A61F 6/225; A61F 6/24
See application file for complete search history.

(56) References Cited

U.S. PATENT DOCUMENTS

2016/0038128 A1* 2/2016 Garrison ............ A61B 17/0401
606/191
2019/0201233 A1* 7/2019 Magno ................ A61L 31/148

* cited by examiner

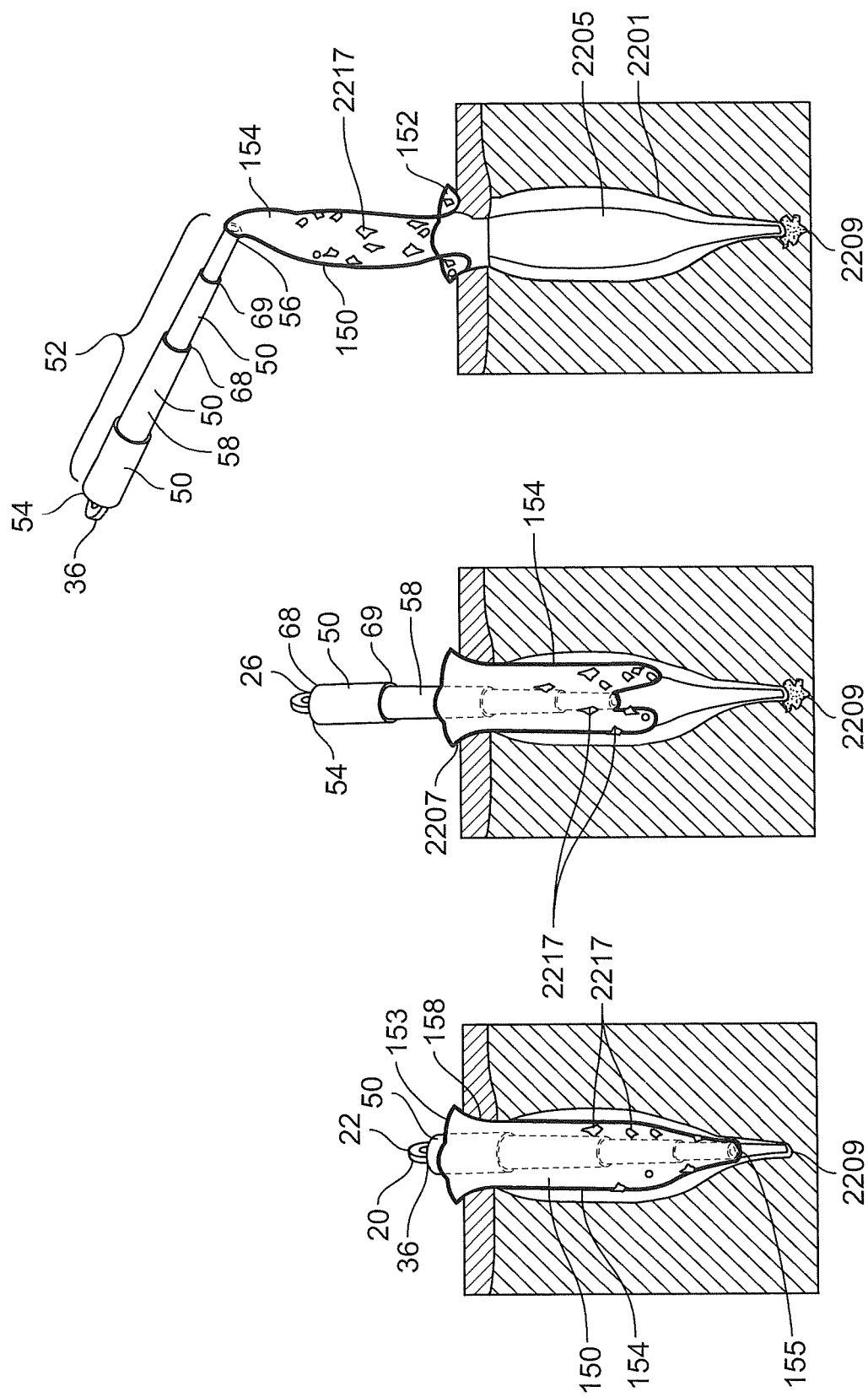

TEMPORARY DRESSING FOR AN INTERNAL WOUND

CROSS-REFERENCE TO RELATED APPLICATIONS

This application is a continuation of U.S. provisional application Ser. No. 62/639,078, filed on Mar. 6, 2018 which is incorporated herein by reference.

BACKGROUND OF THE INVENTION

Blood loss from internal sources causes many deaths and contributes to many more injuries. For example, firearm-related injuries are responsible for more than 34,000 deaths and over 78,000 injuries each year in the United States. Internal blood loss also arises from non-traumatic sources, such spontaneous nose bleeds, hemophilia, and anticoagulant or blood-thinning medications. Where blood loss occurs inside the body, caregivers may have difficulty seeing and treating it. There is a need for dressings that can slow or stop such blood loss by absorbing blood, delivering compressive force to the source of the internal bleeding and/or by delivering therapeutics that encourage clotting to internal bleeding surfaces.

On the battlefield, uncontrolled blood loss is a leading cause of death in soldiers who die in military treatment facilities after sustaining potentially survivable battlefield wounds. Internal wounds are a major source of uncontrolled blood loss, especially when the wounds are inflicted at sites that cannot be treated with traditional methods like direct pressure, dressings, or tourniquets. There is a need for a dressing to slow or stop blood loss from internal wounds that cannot be treated with externally-applied direct pressure, dressings, or tourniquets.

Although the use of tourniquets is believed to increase survival from serious wounds, this treatment is also subject to numerous complications and can cause additional injuries to the nerves, skin, and subcutaneous tissues of an injured person. If a tourniquet is applied for too long or with excessive force, the result can be loss of limb or even death. There is a need for an alternative treatment for internal wounds in place of tourniquets.

Sponges and gauze are sometimes used as temporary dressings to treat blood flow; however, blood-saturated sponges can be difficult to see and sometimes are accidentally left inside a wound cavity after treatment is completed. A further disadvantage is that such temporary dressings provided limited or no compressive force against the internal surfaces of the internal wound. There is a need for an alternative dressing that can be quickly and completely removed from the wound site. Such alternative dressing could decrease the amount of time required for removal, allowing medical care providers to provide substantive treatment more quickly, further enhancing the outcome for the injured person.

A particular difficulty that can arise in the treatment of wounds inflicted by firearms is the unpredictability of the path taken by a bullet after it enters a body. Different types of firearms and different types of ammunition can inflict very different wound profiles. Some firearms deliver a wound with a straight path, while others inflict a generally curving, or yawing, wound path. The composition of the affected tissues and organs can also change the direction or penetration depth of individual wound paths. For example, the wound path can change dramatically when a bullet ricochets against a bone. And where the wound is internal, the precise wound path might not be discernable to an individual rendering medical treatment. There is a need for a dressing that can be applied to firearm wounds with internal wounds paths that cannot be readily seen or predicted.

Other kinds of wounds, such as those inflicted by knives or sharp implements, can become serious or life-threatening problems if the blood loss is not stopped. A common nose bleed can lead to a dangerous loss of blood if it is not stanched in a timely manner. There is a need for dressings to stop hemorrhage in relatively minor internal wounds, before an individual loses a dangerous amount of blood.

Blood-absorbent materials can be readily applied to the surface of a wound, but it is difficult to deliver blood-absorbent materials to internal surfaces of a wound. It can be difficult to deliver a blood-absorbent material, because a treatment device can encounter physical resistance as it is inserted into a wound. Also, as they pass through a wound, liquid-absorbent materials can saturated with wound fluids, further impeding their delivery to the deeper portions of the wound. There is a need for a wound dressing whose absorbent components are kept separate from wound fluids until the device is fully inserted and, once the device is placed into the desired position, the absorbent components can be exposed to the wound liquids throughout the entire wound pathway.

There is also a need for a wound dressing having a shape that provides minimum resistance during its insertion into the wound, until it is fully seated in place, to facilitate the delivery of the device to the desired location. Moreover, it is desirable for the wound dressing to have a shape that minimizes or avoids the infliction of additional injury to the wound path.

In situations where multiple injuries or multiple victims contemporaneously require immediate treatment for firearm injuries, punctures, or other internal wounds, there is a need for wound dressings that can be distributed and applied rapidly. There is also a need for wound dressings that can be applied by the injured individual, or by untrained or minimally trained responders.

BRIEF SUMMARY OF THE INVENTION

The invention relates to a device for stopping blood flow from an internal wound, the device including a handling member connected to a series of successively narrower tubes, providing a generally elongated profile that decreases in width in a stepwise fashion. Each tube or cylinder can include a liquid-expandable article. In some embodiments, the tubes can be pivotably connected to each other, allowing the tubes to conform to the contours of the wound, or fixed together in a rigid or flexible conformation. The tubes can be encased in a liquid-soluble layer that keeps the liquid-expandable article sequestered from liquids until the device is seated within the internal wound.

Upon encountering liquids within the wound, the liquid-soluble layer can dissolve to expose the liquid-expandable article. When exposed to the wound liquids, the liquid-expandable element can expand into an increased volume, providing compressive pressure against the internal wound surfaces and slowing or stopping the flow of blood inside the wound. The tubes and the liquid-expandable element can include additional therapeutic agents for treating the wound.

The temporary dressing can provide therapeutic treatment to internal wounds by several different mechanisms. First, the temporary dressing can provide a physical plug to stop the flow of liquid from the wound, similar to a finger in a dike. Second, the temporary dressing can include expanding elements that provide compressive force against the internal surfaces of the wound, to provide compression against various bleeding arteries, veins, and capillaries that empty into the wound cavity. In this way, the openings of individual blood-carrying vessels can be stopped. Third, for certain vasculature carrying fluid cross the wound path, the device can exert pressure against folded vasculature, and act as a clamp or crimp to halt fluid flow at such sites. Fourth, when manual pressure is applied or the temporary dressing is tied in place, the temporary dressing can create a downward pressure toward the terminus (or exit site) of the wound. Fifth, the temporary dressing can include a therapeutic agent, such as a coagulant compound, that can be delivered to the internal surfaces of the wound site.

The invention relates to a device for insertion into a wound path, the device comprising: a) a member for handling the device, the handling member attached to one of a plurality of connected tubular sections; b) the plurality of connected tubular sections, each tubular section comprising: i) a sidewall surrounding an interior portion, the sidewall including: 1) first and second opposing ends defining first and second mouths, respectively; and 2) a liquid-expandable article that swells into an expanded article upon contact with a liquid; ii) an external flange extending outward from the first mouth, the sidewall defining a periphery of the first mouth; and iii) an internal rim extending inward from the second end, the internal rim defining a periphery of the second mouth; and c) a liquid-soluble layer coating the plurality of connected tubular sections; such that each pair of neighboring tubular sections comprising proximal and distal tubular sections, the external flange of the distal tubular section located within the interior portion of the proximal tubular section, the external flange of the distal tubular section for engaging the internal rim of the proximal tubular section; such that when the plurality of connected tubular sections are inserted into the wound path, the pairs of neighboring tubular sections can move to adopt a shape conforming to a portion of the wound path; and such that when the device is disposed within the wound path, the liquid-soluble layer dissolves upon contacting a liquid in the wound path, exposing the liquid-expandable article to the liquid; and the liquid-expandable article swells into the expanded article upon contacting the liquid in the wound path.

An aspect relates to a device wherein the expanded article exerts a compressive force against an internal surface of the wound path.

Another aspect relates to a device such that each pair of neighboring tubular sections can form an angle between 0-15° in a horizontal plane; and each pair of neighboring tubular sections can form an angle between 0-15° in a vertical plane.

Yet another aspect relates to a device such that when the device is disposed within the wound path, the expanded article provides a compressive force against an internal surface of the wound path.

An additional aspect relates to a device having the pivotably connected tubular section comprising a hollow interior portion.

Another aspect relates to a device including an interior portion comprising a liquid-expandable article.

An additional aspect relates to a device having at least one therapeutic agent chosen from the following: an antiseptic, an antibiotic, an analgesic, an anesthetic, an adhesive, and a coagulant. Yet an additional relates to a device having the liquid-expandable article comprise the therapeutic agent.

Another aspect relates to a device such that: i) in a first portion of the wound path, each pair of neighboring connected tubular sections can adopt a first angle with respect to each other to conform to the first portion of the wound path; ii) in a second portion of the wound path, the neighboring pair of tubular sections can adopt a second angle with respect to each other to conform to the second portion of the wound path; and iii) wherein in a third portion of the wound path, the neighboring pair of tubular sections can adopt a third angle with respect to each other to conform to the second portion of the wound path.

Certain aspects relate to a device comprising a sheath encasing the plurality of connected tubular sections, the sheath comprising a stretchable material for containing the expanded article. Some aspects relate to a device comprising a sheath having a plurality of perforations.

Particular aspects relate to a device including: i) a tip portion, the tip portion comprising the tubular section disposed furthest from the handling member; and ii) a sheath surrounding the plurality of pivotably connected tubular sections, a central portion of the sheath attached to the tip portion, and the sheath comprising an adherent material, the adherent material for adhering to a piece of debris within the wound path; such that upon the removal of the device from the internal wound, the piece of debris remains adhered to the adherent material.

Yet another aspect relates to a kit including the device.

The invention also relates to a device including: a) a member for handling the device, the handling member attached to an elongated portion; b) the elongated portion including: i) a wide end and a narrow end, the handling member proximate to the wide end; and ii) the elongated portion comprising a plurality of cylinders of graduated circumferences that decrease in size in discrete steps, each graduated cylinder comprising a liquid-expandable article that swells into an expanded article upon contact with a liquid; and c) a liquid-soluble coat encasing the elongated portion; such that when the elongated portion is placed within the internal wound, the liquid-soluble coat dissolves upon contact with a liquid within the internal wound, exposing the liquid-expandable article to the liquid; and the liquid-expandable article swells into the expanded article upon contact with the liquid within the internal wound.

An aspect relates to a device such that the expanded article exerts a compressive force against an internal surface of the internal wound.

Another aspect relates to a device including at least one therapeutic agent chosen from the following: an antiseptic, an antibiotic, an analgesic, an anesthetic, an adhesive, and an coagulant. An additional aspect relates to a device having the graduated cylinder comprising the therapeutic agent.

Other aspects relate to a device including a sheath encasing the elongated portion, the sheath comprising a stretchable material; such that when the device is withdrawn from the internal wound, the sheath contains the expanded article proximate to the device.

Certain aspects relate to a device including a sheath encasing the elongated portion, the sheath comprising: a) a central portion attaching to the narrow end of the handling member; b) an peripheral portion surrounding the central portion, the peripheral portion proximate to the handling member; c) an inner surface facing the elongated portion; and d) an outer surface comprising an adherent material, the adherent material for adhering to a piece of debris within the internal wound; such that upon engaging of the handling member to remove of the device from the internal wound, the narrow end of the handling member withdraws the central portion from the internal wound, the central portion withdraws the peripheral portion from the internal wound, and piece of debris remains adhered to the adherent material.

Yet another aspect relates to a kit including the device.

The invention also relates to methods of using the devices to treat internal wounds. Such aspects include a method of treating an internal wound comprising the steps of: a) inserting a wound dressing constructed of a plurality of cylinders that decrease in in size in discrete steps; b) allowing a liquid in the internal wound to dissolve a liquid-soluble coating encasing the cylinders so as to expose a liquid-expandable article; and c) allowing the liquid-expandable article to absorb the liquid in the internal wound so that it conforms to a general configuration of the internal wound and exerts compressive force against an internal surface of the internal wound.

A more detailed explanation of the invention is provided in the following description and claims and is illustrated in the accompanying drawings.

BRIEF DESCRIPTION OF THE DRAWINGS

The accompanying drawings illustrate the present invention and together with the description, further serve to explain the principles of the invention and to enable a person skilled in the relevant art to make and use the invention.

These and other features and advantages of the present invention will be apparent from the following detailed description, claims, and accompanying drawings.

FIG. 1A shows a perspective view of the device; FIG. 1B shows a perspective view of another device; FIG. 1C shows a side view of a device; and FIG. 1D shows a cross-sectional view of the device.

FIGS. 2A-2B show side and perspective views of an embodiment of a tubular section; FIGS. 2C-2F show side, perspective, cross-sectional, and top views of another embodiment of a tubular section.

FIG. 3A shows that the tubular sections can pivot to change their configuration with respect to each other, allowing the plurality of tubes to communicate with the inner surfaces of the wound. FIG. 3B shows a device where, in the presence of fluids within the wound site, the liquid-expandable articles have increased in volume and become expanded articles; the expanded articles can apply compressive force against the internal surfaces of the wound.

FIG. 4A shows a temporary dressing with a close-fitting sheath, prior to insertion of the device into a wound. FIG. 4B shows a temporary dressing with one or more expanded absorbent elements contained within the sheath; here, the sheath is made of a material that allows it to stretch as the absorbent elements expand, keeping the expanded absorbent elements confined to the device. FIG. 4B also shows that the individual tubular sections can pivot with respect to neighboring tubular sections, allowing the temporary dressing to adopt a configuration that conforms to the shape of the wound path.

5A-5C show views of another embodiment of a temporary dressing having multiple cylindrical sections fixed in place with respect to each other, with the temporary dressing including a sleeve or sheath covering the device. The sheath can cover the outer surface of device, with a central portion of the sheath attached to a lower tip portion of the device, and can include a material that can attract and adhere bits of debris or foreign matter present in the wound. FIG. 5A shows the sheathed device placed within an internal wound. FIG. 5B shows the device that has been partially withdrawn from the internal wound, the withdrawal of the device causing the sheath to start turning outside-in. FIG. 5C shows the sheathed device being withdrawn from a wound, the debris adhering to the sheath and being drawn out of the wound when the sheath exits the wound path.

FIG. 8A shows the devices deployed within the wound, with a device being inserted into an entry wound and exit wound of the injury. FIG. 8B shows the devices after the liquid-expandable articles have absorbed liquid within the wound and expanded into expanded articles, with the sleeves containing the expanded articles within the devices.

FIG. 9A shows that the temporary dressing can apply outward, compressive pressure on the interior surfaces of the wound. FIG. 9B shows that the elongated, stepwise shape of the temporary dressing can include elements that absorb liquid and expand to apply outward or sideward pressure against the exposed surfaces of the internal wound cavity. FIG. 9C shows that, near the wound pathway, the ends of severed blood vessels can be folded, so that an expanding portion of the device can crimp the blood vessels partially or wholly shut. FIG. 9D shows that the temporary dressing can include a therapeutic agent, such as a coagulant compound, that can be dispensed into the wound site.

DETAILED DESCRIPTION OF THE INVENTION

Figure 1A:
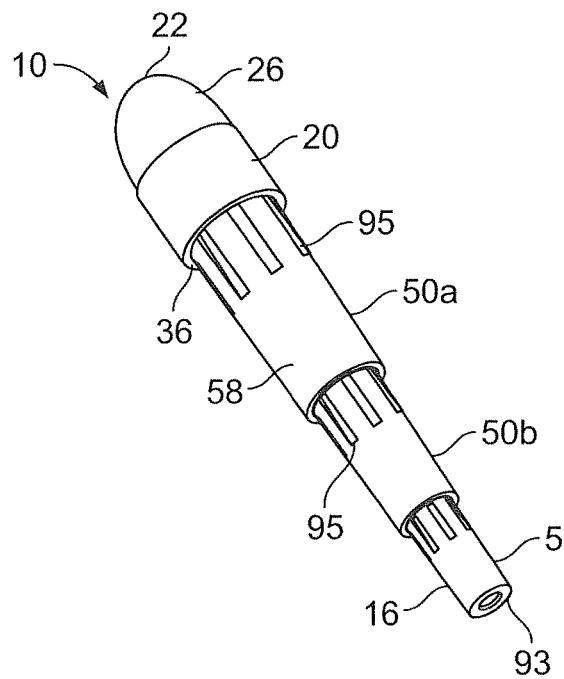
FIGS. 1A-1D show views of an embodiment of a temporary dressing device for an internal wound, an embodiment that includes a generally elongated portion including multiple tubular sections that are connected to each other in a fashion allowing pivoting movement.
Figure 1B:
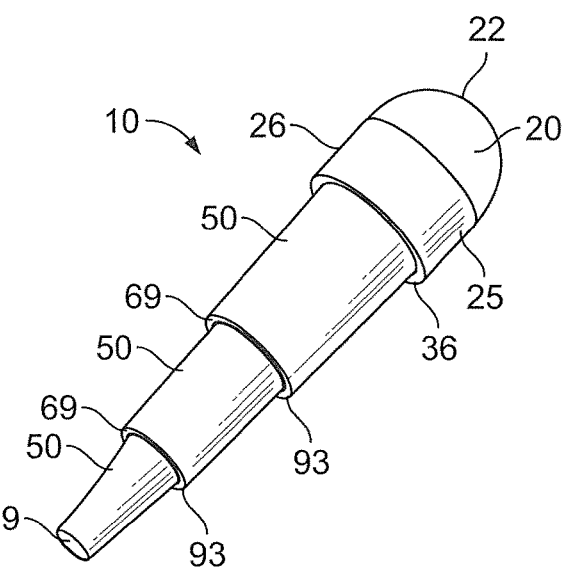

While this invention is susceptible of embodiments in many different forms, there are shown in the drawings and will be described in detail herein specific embodiments with the understanding that the present disclosure is to be considered as an exemplification of the principles of the invention. It is not intended to limit the invention to the specific illustrated embodiment.

The features of the invention disclosed herein in the description, drawings, and claims can be significant, both individually and in any desired combinations, for the operation of the invention in its various embodiments. Features from one embodiment can be used in other embodiments of the invention.

It should be further understood that the title of this section of this specification, namely, "Detailed Description Of The Invention," relates to a requirement of the United States Patent & Trademark Office, and does not imply, nor should be inferred to limit the subject matter disclosed herein.

In the present disclosure, the words "a" or "an" are to be taken to include both the singular and the plural. Conversely, any reference to plural items shall, where appropriate, include the singular.

Referring to the Figures, FIGS. 1-9 show embodiments of a medical device 10 for use as a temporary dressing for internal wounds 2201 shown in accordance with the present invention.

Typical wounds can include a cavity 2205 within an individual, the cavity 2205 communicating with the surface of the body of the individual via an entry wound 2207 site, with blood flowing or seeping from one or more surfaces of the cavity 2205. The wound can terminate with the cavity 2205, or can travel through the body to terminate in one or more exit wounds 2211. The entrance wound 2207, cavity 2205, and exit wound 2211 (where there is one) communicate with the interior surfaces of the wound path 2201.

Exemplary wounds 2201 often arise from, but are not limited to, traumatic accidents, stabbing wounds from knives, projectiles from weapons (particularly bullets from firearms) or improvised explosive devices, as well as nose bleeds. The device 10 can be used on wounds 2201 characterized by small or broad entrance wounds 2207, where the wounds provide a medical responder with limited or no visibility to the sites of non-compressible, internal bleeding.

Referring to the Figures, embodiments of a medical device 10 for use as a temporary dressing for internal wounds are shown in accordance with the present invention. The invention relates to a device 10 including a handling member 26 connected to a series of linked tubes 50 or cylinders. Each successive tube 50 can have a smaller diameter than its predecessor, giving the device 10 a generally tapering profile, and can include a liquid-expandable article 118 for absorbing the fluids present in the wound path. In some embodiments, the tubes 50 can be connected to each other to allow neighboring tubes to pivot or rotate with respect to each other; such tubes could allow neighboring tubes to change their positions with respect to each other, to achieve a range of angles or positions as needed. In other embodiments, the tubes 50 can be fixed together so that they cannot move with respect to each other; such plurality of tubes can be rigid and unmoving, or flexible. The device can 10 include a liquid-soluble coating 124 (or layer or film) to sequester the liquid-expandable articles 118 away from liquids until the device 10 is disposed into the wound cavity 2205. Then the liquid-expandable article 118 can absorb the liquid present in the wound path and expand in volume to provide an expanded article 120. The expanded article 120 can encourage a slowing or stopping of blood loss by, for example, compression delivered internally to the wound 2201 site, providing structures or surfaces to promote coagulation, or delivering therapeutic agents 104 to promote hemostasis.

Optionally, the device 10 can include a sheath or sleeve 150 encasing the device 10; such sleeve 150 can comprise materials that help the device to traverse the wound path smoothly or to apply a medical agent 104 or treatment to the internal wound.

Embodiment 1: Temporary Dressing with Pivotable Tubular Sections

As shown in FIGS. 1-2, the device 10 can include a handling member 26 by which an individual can grasp the device 10. This handling member 26 can provide a means for the individual to insert the device 10 into an internal wound 2201; it can provide a means for an individual to manipulate or guide the device; and it can provide a means for the individual to withdraw the device 10 from the internal wound 2201.

The handling member 26 can be provided by a base portion 20. It is preferred that the widest portion of the base portion 20 have a width equal to or larger than a width of any of the tubes 50. The base portion 20 can be tubular or cylindrical in shape; it is preferred that the base portion 20 have a shape similar to that of the tubes 50.

The base portion 20 can have a first side 22 facing a plurality of tubes 50, and a second side 36 opposite the first side 22. The second side 36 can be positioned to rest in a location proximate to a site where the internal wound 2201 meets an external surface of the wounded individual's body (e.g., entry wound 2207 or exit wound 2211). When the device 10 is secured, the second side 36 can protrude from the internal wound 2201, be flush with the external surface of the body, or be seated within the internal wound 2201.

The second side 36 of the base portion 20 can include, for example, a flat surface or a curved dome, although a convex shape is preferred. The second side 36 can be smooth, textured, rough, or contoured.

The first side 22 of the base portion 20 can be connected or joined to a plurality of tubular sections or tubes 50.

The plurality of tubular sections or tubes 50 can be connected to each other, preferably end-to-end, such as is shown in FIGS. 1 and 3. The tubes 50 can have a generally or overall cylindrical shape, although the tubes can be fashioned in other shapes, to have cross-sections that rectangular, trapezoidal, triangular, or other shapes, such as shown in FIGS. 2A-2F. The tubes 50 can have a uniform cylindrical shape having the same diameter at its first end 68 (the end nearest the base portion 20), its opposed second end 69 (end furthest from the base portion 20) and throughout the length of the tube 50.

Each tube 50 can have sidewall 58 with a diameter that is greater than the diameter of each successive tube 50, so that the diameters of the tubes 50 decrease over a length of the device 10. The first tube 50a in the series can have a first sidewall diameter, the second tube 50b can have a second sidewall diameter smaller than the first diameter, the third tube 50c (if there is one) can have a third sidewall diameter smaller than the second diameter, and each successive tube 50 (if there are successive tubes 50) can have a smaller sidewall diameter than its immediate predecessor. For each pair of neighboring tubes 50, the difference in sidewall diameter can be the same length or a different length. In some embodiments, for every pair of neighboring tubes 50, the ratio between the sidewall diameter of the first, larger tube 50 and the sidewall diameter of the second, smaller tube 50 will be the same.

Taken together, the plurality of tubes 50 can have a profile that narrows from a broader or wider first end 54 to a narrower second end 56, such as is shown in FIGS. 1A-1D. When viewed in profile, such as in FIG. 1D, the device 10 have a plurality of tubes 50 that narrow in discrete steps, providing a profile that narrows in a stepwise, stepped, or terraced fashion. In some embodiments, such stepwise configuration can facilitate a degree of compression in each tube or tubular section 50, allowing the device 10 to be compressed against a firm or stable surface (e.g., a bone).

Figure 1C:
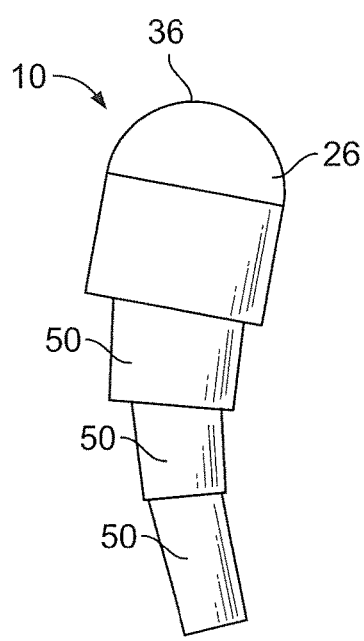
Figure 1D:
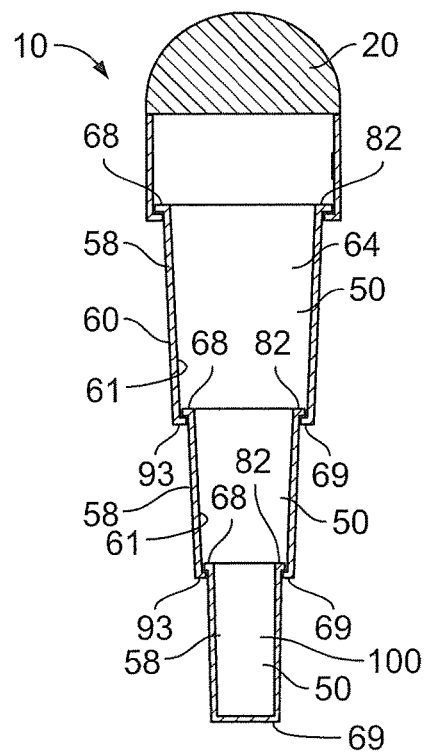
Figure 2A:
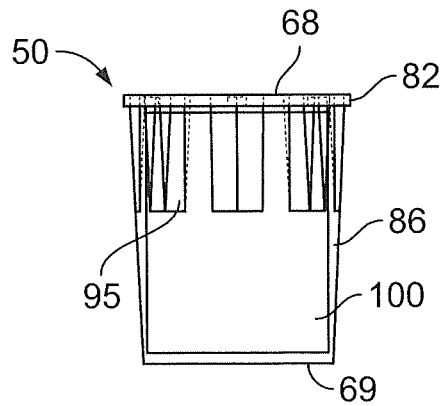
FIGS. 2A-2F show views of individual tubes or tubular sections found in some embodiments of the temporary dressing.
Figure 2B:
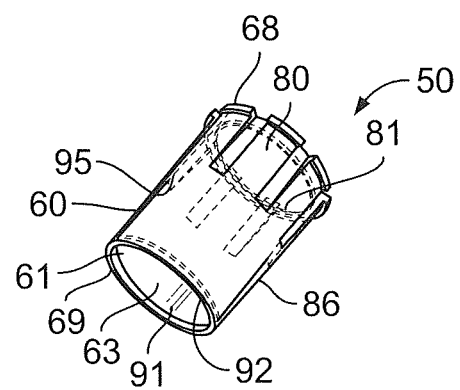
Figure 2C:
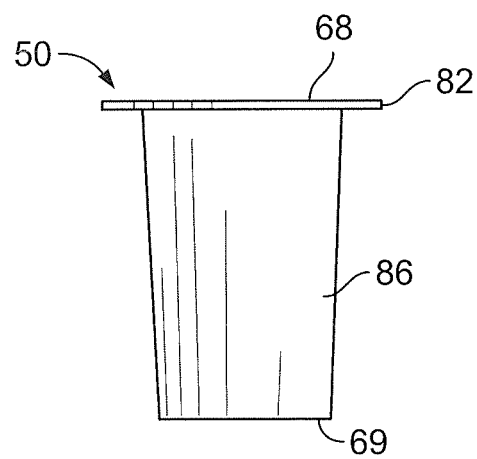
Figure 2D:
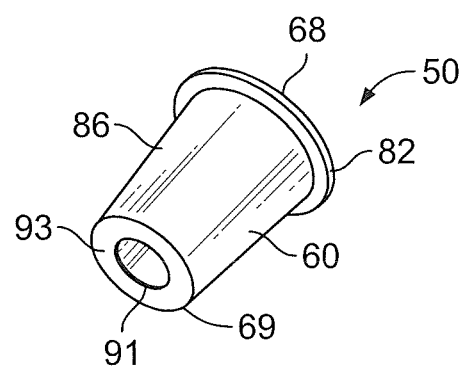
Figure 2E:
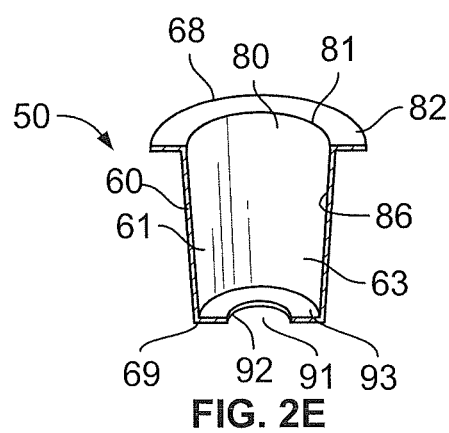
Figure 2F:
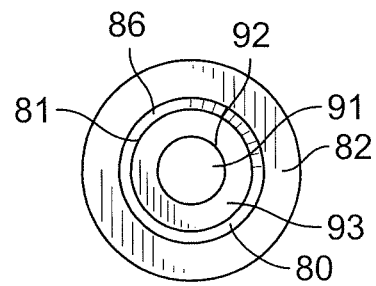

The device 10 can have a smoothly tapering profile, or in a preferred cross-sectional view can show a decrease in tube 50 width in a stepwise fashion, such as shown in FIG. 1D. In embodiments where the tubes 50 have a cross-section that is other than circular or round, the each successive tube 50 can have a circumference or perimeter that is smaller than its predecessor. In some embodiments, individual tubes can include protrusions or bulges on their outer surfaces, creating a profile that is generally, but not perfectly, tapering or tiered or terraced.

Each tube 50 can have the same length or can have different lengths, or a mixture of same and different lengths. In some embodiments, each successive tube 50 can have a greater (or shorter) length than its predecessor. In some embodiments, each successive tube 50 can have both a smaller diameter and a smaller length than its predecessor.

Figure 3A:
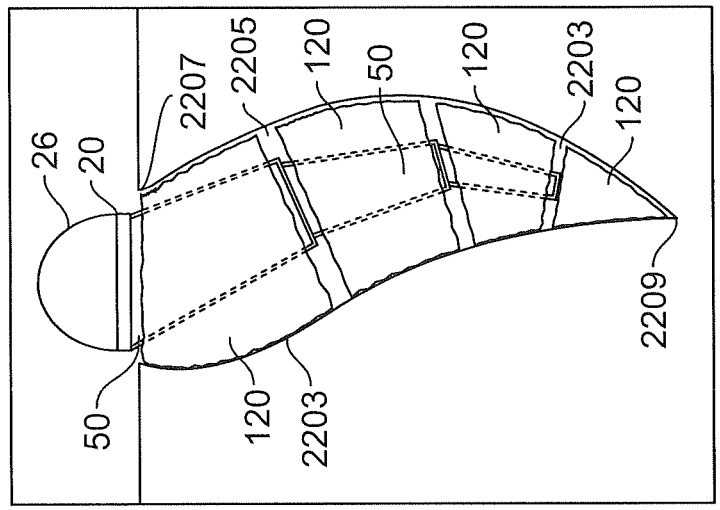
FIGS. 3A-3B shows views of a temporary dressing seated within a wound site.
Figure 3B:
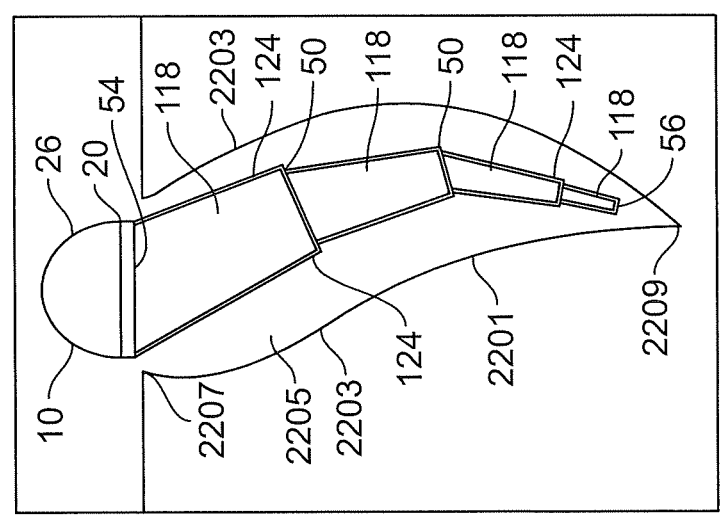

Each tube or tubular section 50 can include a central longitudinal axis. All of the tubes 50 can be aligned along the same central longitudinal axis, such as shown for example in FIGS. 1A-1B. The base portion 20 can include a central longitudinal axis which can be aligned along the same central longitudinal axes of the tubes 50; in such an alignment, the plurality of tubes 50 can possess a profile that is symmetrical in one or more, or all cross-sections taken through a central longitudinal axis. However, the plurality of tubes 50 can have pivoting connections to each other than allow the tubes 50 to adopt configurations not aligned along the central longitudinal axis, such as shown in FIGS. 1C and 3A-3B.

Each tube 50 can include a sidewall 58, a surface that can surround a hollow portion 63, the sidewall 58 having first and seconds mouths 80, 91 positioned at first and second ends 68, 69 of the tube 50, respectively, as shown for example in FIGS. 2A-2F. The first end 68 of each tube 50 can be positioned closer to the base portion 20 than the second end 69 of the tube 50. The first mouth 80 of each tube 50 can be positioned closer to the base portion 20 than the second mouth 91 of the tube 50. Neighboring tubes 50 can connect or join end to end, a second end 69 of one tube (e.g., 50a) adjoining the first end 68 of the neighboring tube (e.g., 50b), such as shown in FIG. 1D.

As shown in FIGS. 2A-2F, each tube 50 can include an external flange 82 extending outward from the periphery 81 of the first mouth 80; the external flange 82 can extend outward from the exterior surface 60 of sidewall 58. The flange 82 can extend outward substantially perpendicular to the sidewall 58. The external flange 82 can include a solid disk covering the first mouth 80; the external flange 82 can have one or more openings or perforations defined in the external flange 82, or the external flange 82 can have one or more openings arranged around the periphery of the external flange 82.

Each tube 50 can include an internal retaining rim 93 extending inward from the interior surface 61 of the sidewall 58, the retaining rim 93 defining the periphery 92 of the second mouth 91. The internal retaining rim 93 can define a flat surface or ledge-like structure providing a partial boundary around the periphery or outer edge 86 of the second mouth 91, near the second end 69 of the tube 50, so that the opening defined by the second mouth 91 has a smaller diameter than the diameter of the tube's sidewall 58.

For each tube 50, the diameter defined by the outer edge of the external flange 82 can be greater than the diameter of the sidewall 58, and the diameter of the sidewall 58 can be greater than the diameter of the second mouth 91, and a central longitudinal axis of the tube 50 can pass through the centers of one or all of these structures 50, 82, 58, 93.

Each sidewall 58 can include a solid surface or a surface with pores, or openings; such openings can provide a structure for delivering or dispensing a therapeutic agent 104 from the device 10.

Each tube 50 can further include one or more grooves 95 in the exterior surface 60 of the tube 50. The grooves 95 can extend from the first end 68 of the tube 50. The grooves 95 can extend to the second end 69 of the tube 50 or terminate at some point before reaching the second end 69. The grooves 95 can run substantially perpendicular to the external flange 82 and/or the planes defined by the first or second mouths 80, 91; alternatively, the grooves 95 can run at an angle (preferably other than a right angle to the external flange 82) around the exterior surface 60 of the tube 50. Each groove can define a channel or furrow on the outer surface 60 of the sidewall 58. Preferably, the grooves 95 can run parallel to each other on the exterior surface 60 of the tube 50.

Each groove 95 can communicate with an opening or perforation in the external flange 82. Each groove 95 can define a cut-out section 89 in the external flange 82, such that the external flange 82 defines a crenellated outer edge 86 around the external flange 82. That is, the external flange 82 can have spaced-apart sections 89 removed from its outer edge 86 (i.e., cut-outs), or in the alternative, have spaced-apart sections protruding outward (or inward) from its outer edge 86. The spaced-apart sections can have shapes that are square, rectangular, polygonal, or some other shape.

Each crenellation, or outwardly-protruding section 85, can include a protrusion 87 on its outer edge 86, also extending outward, called an outwardly-protruding section. Each outwardly-protruding section can be arranged in a radial fashion around the external flange 82, with each protrusion 87 arranged on the outer surface of the outwardly-protruding section to accentuate a radial (or sunburst) appearance in the external flange 82.

In the absence of the grooves 95, the external flange 82 can have a smooth, regular, uninterrupted outer edge 86.

Each tube 50 can include an internal compartment 100 within the tube 50, the internal compartment 100 containing one or more therapeutic agents 104. Such internal compartment 100 can be defined by the sidewall 58 of the tube 50 or occupy a smaller interior space within the tube 50. The internal compartment 100 can include first and second barriers on opposite ends, enclosing it from the first and second mouths 80, 91, respectively. The internal compartment 100 can contain one or more therapeutic agents 104, such as antibiotics, analgesics, coagulants, and saline solution.

As shown in FIGS. 1 and 3, each pair of tubes 50 can connected to each other in a fashion allowing for pivoting movement between the tubes 50. The external flange 82 of the second tube 50b can be positioned within the hollow portion 63 of the first tube 50a, with the internal retaining rim 93 keeping the external flange 82 of the second tube 50b contained within the first tube 50a. In some embodiments, a portion of the second tube 50b can move within the hollow portion 63 of the first tube 50a, allowing the tubes 50a, 50b to pivot with respect to each other at that juncture of the tubes.

Each pair of tubes 50 can also be defined as including: i) a proximal tube (e.g., 50a), or tube closest to the base portion 20 or tube closest to the handling member 26; and ii) a distal tube (e.g., 50b), or tube furthest away from the base portion 20 or tube furthest away from the handling member 26. Each pair of proximal and distal tubes can be connected to each other to enable pivoting movement with respect to each other.

An upper portion of the distal tube 50, proximate to its first mouth 80, can be disposed within the cavity or hollow portion 63 of the proximal tube, with the sidewall 58 of the distal tube 50 passing through the opening in the distal end of the proximal tube 50. The outward-extending external flange 82 of the distal tube 50 can engage the inward-extending internal retaining rim 93 of the proximal tube 50, preventing the distal tube 50 from disengaging from the proximal tube 50.

The second tube 50*b* can have an external flange 82 and diameter of a size to allow the tubes 50 to pivot, so as to adopt an angled (non-straight) configuration with respect to each other, or with respect to the longitudinal axis of each tube 50. It is preferred that one or more (or all) of the tubes 50 be able to move or pivot to adopt a range of angles so that the device 10 can curve or bend to follow the contours of a wound having an angled or bending, or meandering path. Such conformation could be preferred for a bullet wound with an irregular ricochet path, as particularly shown in FIGS. 3A-3B.

Each pair of neighboring tubes 50 can move with respect to each other in both a horizontal direction and a vertical direction (when the device 10 is oriented so that it has a central longitudinal axis is perpendicular to the ground). Each pair of neighboring tubes 50 can move between a range of angles with respect to each other in the horizontal and vertical directions or planes (or x- and y-planes), or move between 0-45°, 0-30°, 0-15°, 0-10°, or between 1-45°, 1-30°, 1-15°, 1-10°. Because of the ability to alter relative positions in at least two dimensions, each pair of neighboring tubes 50 can adopt a large number of positions with respect to each, and can be positioned to adopt the position necessary for the portion of the wound 2201 that they communicate with. More each pair of neighboring tubes 50 can For each pair of neighboring tubes 50 comprising a proximal and distal tube 50*a*, 50*b*, the external flange 82 of the distal tubular section 50*b* can be located within the interior or hollow portion 63 of the proximal tubular section 50*a*, with the external flange 82 of the distal tubular section 50*b* pivotably engaging the internal retaining rim 93 of the proximal tubular section 50*a*.

When the plurality of pivotably connected tubular sections 50 are inserted into the wound path 2201, the pairs of neighboring tubular sections 50*a*, 50*b* can pivotably move to adopt a shape conforming to a portion of the wound path 2201. As the device 10 moves through the wound path, the pairs of neighboring tubular sections 50*a*, 50*b* can pivotably move to adopt different orientations relative to each other to conform to whichever portion of the wound path 2201 they contact.

Because the connection between each pair of neighboring tubes 50 is a pivoting connection, the wound plug device 10 can adopt angles in x-, y-, and z-dimensions, allowing the device 10 to travel along a pathway that is straight, curved, angled, spiraling, non-linear, or irregular in all three-dimensions or planes. Such a device 10, with its pivotably connected tubular sections or tubes 50, can engage a wound path that changes direction one or all of the x-, y-, and z-dimensions or planes; it is not limited to following only a path that is straight in one or more of these dimensions or planes.

The base portion 10 can attach to the plurality of tubes 50 by any means known in the art. For example, the external flange 82 of the first tube 50*a* can be attached or affixed to the base portion 20. In other embodiments, the base portion 20 can snap onto the first tube 50*a*, or the base portion 20 can comprise an internal thread on its internal surface, which can engage an external thread on the exterior surface 60 of the sidewall 58 of the first tube 50*a*.

As shown, for example in FIGS. 3A-3B, each tube 50 can include one or more liquid-expandable articles 118 capable of expanding into an expanded article 120 upon contact with a liquid, such as blood, serum, or other bodily fluid. In some embodiments of the invention, the volume of the liquid-expandable article 118 can experience, for example, a 2-fold increase, a 10-fold increase, a 100-fold increase, a 1,000-fold increase, a 10,000-fold increase or greater. That is, a volume of the expanded article 120 can be at least 2, 10, 12, 50, 100, 1,000, or 10,000 times larger than a volume of the corresponding liquid-expandable article 118.

Each tube 50 can include one or more liquid-expandable articles 118 as a component within a sidewall 58. In some embodiments, the sidewall 58 can be comprised of one or more liquid-expandable articles 118. In some embodiments, one or more liquid-expandable articles 118 can be attached to an exterior surface 60 of the sidewall 58. In some embodiments, the sidewall 58 can be comprised entirely of one or more liquid-expandable articles 118.

When the device 10 is disposed within a wound path 2201 or a wound cavity 2205, the liquid-expandable article 118 can expand into an expanded article 120 that is large enough to provide compressive force against internal bleeding surfaces of the wound path 2201. However, the expansion process can be gentle enough so that foreign objects in the internal wound 2201 (i.e., bullets, bullet fragments, bone shards) are surrounded by the expanded article 120, rather than forced against the wound 2201 site.

The liquid-expandable article 118 can absorb the liquid present in the wound path and expand in volume to provide an expanded article 120. The expanded articles 120 can form a plug that expand to fill the defect or void space defined by the wound 2201. The expanded articles 120 can encourage a slowing or stopping of blood loss by, for example, via delivering compression against internal surfaces of the wound 2201 site. Much as the device 10 can serve to plug the wound 2201, the expanded articles 120 can provide plugs against individual arteries, veins, and other vasculature.

The liquid-expandable articles 118 can provide structures or surfaces to promote coagulation within the wound cavity 2205. The liquid-expandable articles 118 can also provide a vehicle for delivering therapeutic agents 104 into the wound cavity 2205 to promote hemostasis.

Figure 6A:
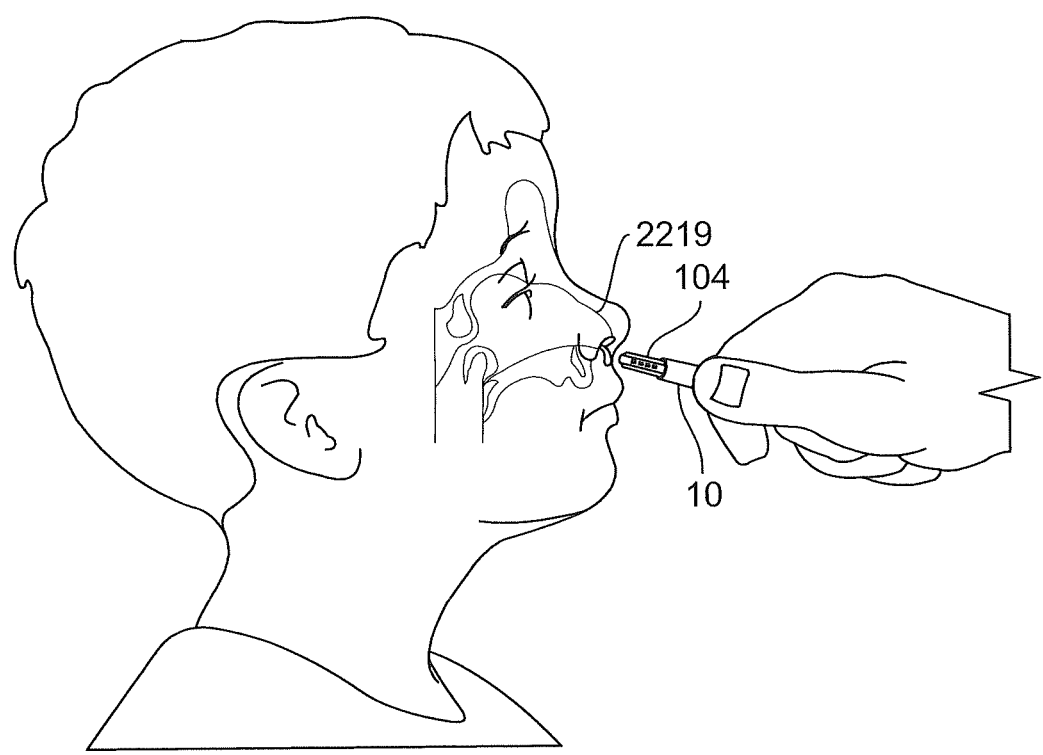
FIGS. 6A-6B show the temporary dressing containing a therapeutic agent before and after being applied to a nose bleed, respectively.
Figure 6B:
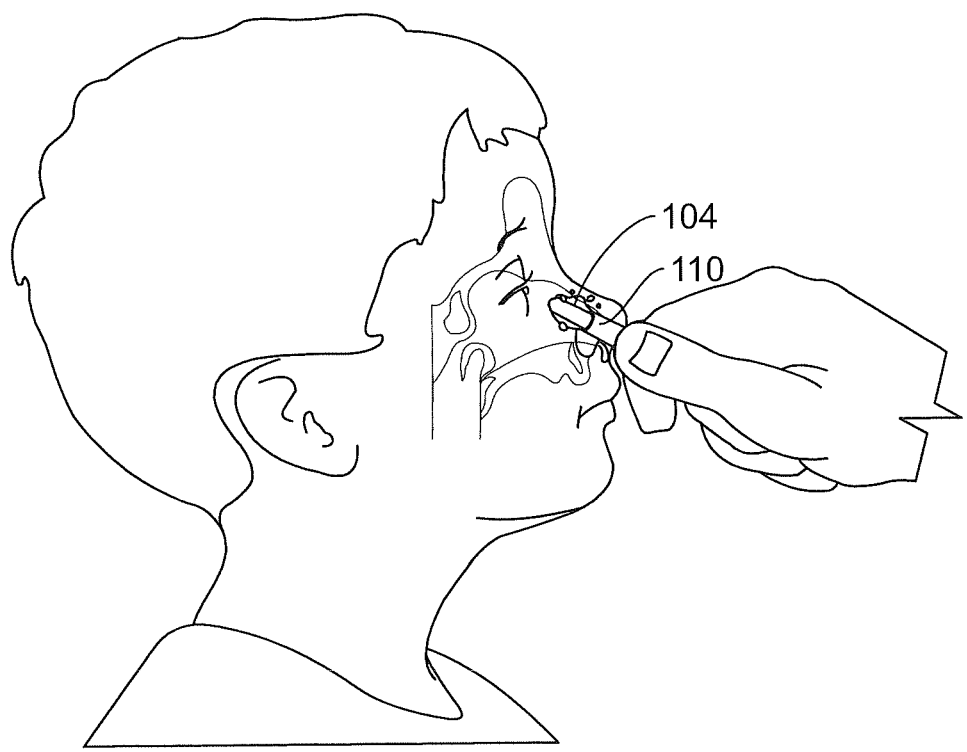

In some situations, the tubes 50 can comprise a plurality of liquid-expandable articles 118. The expanded article 120 can have a predetermined shape so that the expanded article 120 adopts a shape predicted to expand, partially or completely fill, and conform to the shape of the wound cavity 2205 of a particular type. For example, the size and directions of the paths of bullet wounds have been extensively studied and characterized. An individual treating a bullet wound can choose to apply a device 10 having a shape and size designed for conforming to bullet wounds, as shown in FIGS. 3-4. An individual with a nose bleed can be treated with a device 10 with sized and shaped for optimal treatment of a bleeding sinus cavity 2219, as shown in FIGS. 6A-6B.

As shown in FIGS. 3A-3B, the device can 10 include a liquid-soluble coating 124 to sequester the liquid-expandable articles 118 away from liquids until the device 10 is disposed into a desired location and position inside the wound cavity 2205. The liquid-soluble coating 124 can prevent the premature exposure of the liquid-expandable articles 118 to fluids within the wound path 2201. Thus, the device 10 can maintain its relatively narrow profile (compared to the wound path 2201) and relatively compact shape (compare FIGS. 3A and 3B) to move freely through the wound path 2201 until reaching the terminus 2209 of the wound 2201 or other desired position. Also, when the liquid-expandable articles 118 absorb fluid and become expanded articles 120, they experience a radical increase in volume. Prematurely expanded articles 120 may provide blockage that impedes the insertion of the device into the deeper, more distal regions of the wound 2201. The liquid-soluble coating 124 can be compounded to dissolve at a preferred rate or at a preferred time, particularly after exposure to liquids such as found in a wound 2201. Alternatively, the liquid-soluble coating can be applied in a thickness that will facilitate its dissolution at a desired speed, time, or rate.

In some embodiments, the liquid-soluble coating 124 can comprise a polymer film containing reagents that dissolve at predetermined rates when in contact with a biological fluid or other liquid. In some embodiments, the liquid-soluble coating 124 can comprise hydrophilic or hydrophobic coatings or layers of polymers or copolymers. The liquid-soluble coating 124 can be made of gelatin, chitosan, hydrogel, synthetic polymers such as polyvinyl alcohol, polyurethanes, polyethylene glycol, alginates, hydrocolloids, or other water-soluble material, or combinations thereof. Preferably, the liquid-soluble coating 124 is made of a material known to be compatible with biological systems, that can be dissolved by fluids typically found within wounds 2201 (e.g., blood or sera).

Preferably, the liquid-soluble coating 124 will provide a continuous layer surrounding the outer surfaces (e.g., 60) of the tubes or cylinders 50, though the liquid-soluble coating 124 can also include openings, slits, or areas having a thinner layer of coating, to promote its dissolution or to promote dissolution in a desired location- or time-dependent manner.

It is preferred that the liquid-soluble coating 124 provide a non-stick surface when inserted into a wound or provides a surface with lubricant properties, to ease the insertion of the device 10 into a wound. The liquid-soluble coating 124 can comprise a therapeutic agent 104, particularly a therapeutic agent 104 with a coagulant, absorptive, or antimicrobial properties.

The liquid-soluble coating 124 can provide a continuous layer separating the device 10 from liquids present in a wound path, as well as provide protection against environmental sources of liquid, such as ambient humidity.

One or more of the tubes 50 can connect directly or indirectly to an optional sleeve or sheath 150, as shown in FIGS. 3A-3B.

Optional Feature: Sleeve

As shown in FIGS. 4-5, 8B, and 9, the device 10 can include a sleeve 150 that provides an external covering for the device 10. The sleeve 150 can include a thin sheet of non-stick material to cover the outer surfaces of the base portion 20 and plurality of tubes 50. The sleeve 150 can cover plurality of tubes 50 from its broader or wider first end 54 to its narrower second end 56.

In some embodiments, the sleeve 150 can cover only the outer surfaces of the plurality of tubes 50. An inner surface 152 of the sleeve 150 can face or contact the outer surfaces of the base portion 20 and plurality of tubes 50, while an outer surface 154 of the sleeve 150 (opposite the inner surface 152) can face away from the device 10 and toward the surfaces 2203 of the internal wound 2201.

The sleeve 150 can include a peripheral portion 153 surrounding a central portion 155. In some embodiments, the peripheral portion 155 can be proximate or attached to the base portion 20, while the central portion 155 can be attached to one or more of the plurality of tubes 50. In some embodiments, the central portion 155 can be attached to the tube 50 that is furthest from the handling member 26 (e.g., a tip portion 16 of the device 10); such central portion 155 can be attached to the tip of the plurality of tubes 50, at the narrow end 56 of the plurality of tubes 50.

The height or length of the sleeve 150 can be greater than, equal to, or less than height or length of device 10. The radius of the sleeve 150 can have a length greater than a length of the device 10, as measured along a longitudinal axis of the device 10. In some embodiments, the distance between attachment site on device 10 and an peripheral edge of the sleeve 150 can have a length greater than a length of the device 10; there, any the peripheral portion 153 of the sleeve 150 can be disposed around the exterior surfaces of the wound, and can provide a covering over the external wound site (e.g., 2207).

The sleeve 150 can include a fabric or film encasing the outer surface of the device, particularly encasing the plurality of tubes 50. The sleeve 150 can be fitted or contoured to closely conform to the outer surface of the base member 20 and plurality of tubes 50.

The sleeve 150 can have an opening or mouth 158 that encircles or surrounds the base portion 20 or tubes 50. When the device 10 is fully seated within the wound 2201, the sleeve can separate the device 10 from the wound 2201. Here, the sleeve 150 can comprise pores 157 or openings to allow blood or fluid the contact the device 10. It is preferred that the sleeve 150 be of a size to accommodate the transition of the liquid-expandable article 118 into an expanded article 120 without rupturing the sleeve 150.

Figure 8B:
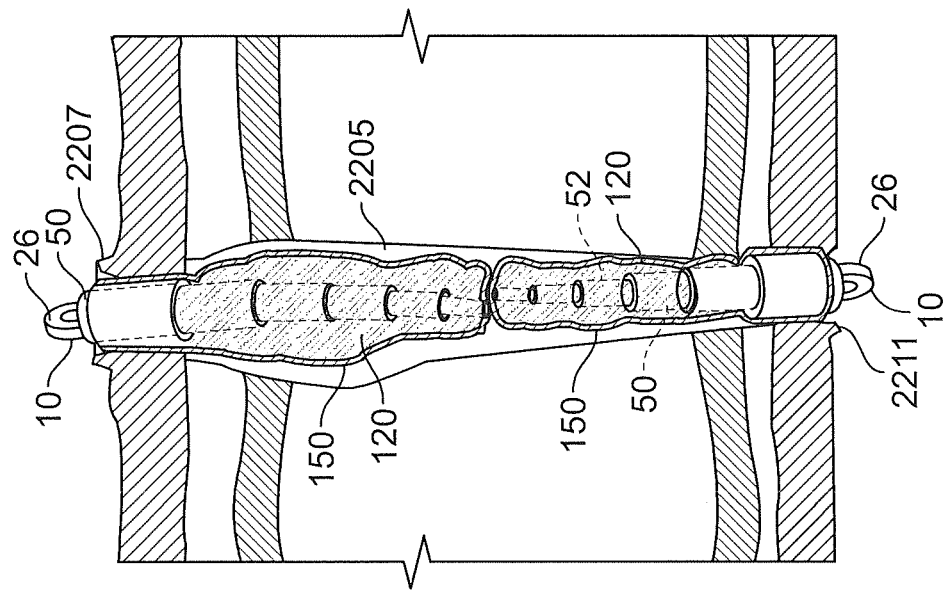
FIGS. 8A-8B show temporary dressings with sleeves used to treat a through-and-through injury to a limb, such as an arm or leg.

The sleeve 150 can be deformable, can comprise a material that is stretchable, to accommodate the expanding absorbent materials 120; that is, it can stretch or expand to keep the expanded articles 120 contained within the sleeve 150, so that the expanded articles 120 do not migrate away from the device 10 and into the wound cavity 2205. That is, the sleeve 150 can keep the expanded articles 120 close or proximate to the device 10 while the device 10 is in the wound 2201 and when the device 10 is withdrawn from the wound 2201, such as shown in FIGS. 4A-4B and 8B.

Figure 4A:
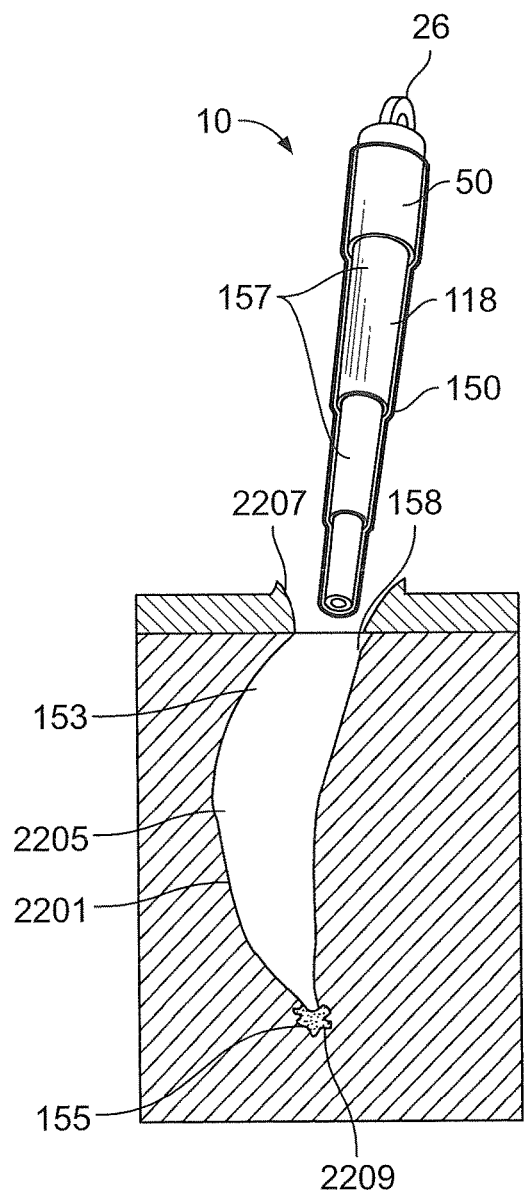
FIGS. 4A-4B show views of an optional feature of the temporary dressing: a sheath or sleeve covering the temporary dressing.
Figure 4B:
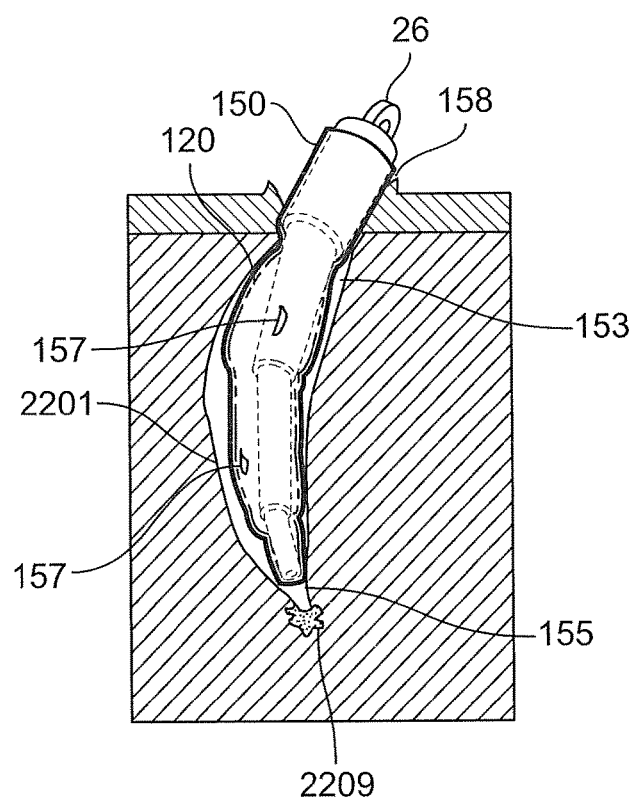

In some versions, the sleeve 150 can provide a snugly-fitting cover to the device, such as shown in FIG. 4A.

The sleeve 150 can be attached to the device 10, unattached to the device 10, or detachable from the device 10.

In some embodiments, the sleeve 150 can be attached to the plurality of tubes 50. For example, the sleeve 150 can be attached to the plurality of tubes 50 at its broader or wider first end 54 or can be attached to the plurality of tubes 50 at its narrower second end 56. Where the sleeve 150 is attached to a tube 50, the sleeve can be attached to the external flange 82, internal retaining rim 93, second mouth 91, or exterior surface 60 of sidewall 58 of the tube 50.

When the device 10 is inserted into a wound path, an outer surface 154 of the sleeve 150 can engage an inner surface 2203 of the wound 2201. Here, the device 10 is contained within the sleeve 150. In some embodiments, the all or a portion of an end 54, 56 of the plurality of tubes 50 can be positioned outside of the sleeve 150.

Where the sleeve 150 is attached to the narrower second end 56 of the tubes 50, the base portion 20 can be pulled or manipulated to dislodge or disengage the tip portion 16 from its engagement with the inner surface 2203 of the wound 2201, such as shown in FIGS. 5A-5C. This can be especially advantageous for removing the device 10 after an expanded article 120 has generated strong compressive force or even a seal against the inner surface 2203 of the wound 2201. This feature allows for gentle disengagement from the wound 2201, to minimize damage to the wound 2201 when the device 10 is removed.

It is preferred that the sleeve 150 be made of a non-stick material that can have pores 157 or openings or perforations, such as TELFA™ bandages or dressings. The sleeve 150 can be made of a slick, non-sticking material, to prevent the device from catching on irregular wound surfaces, cellular debris 2217, bone or tissue fragments, torn muscle, damages organs and the like. The sheath 150 can include a lubricant to facilitate the smooth entry of the device 10 into the wound. It is preferred that the sleeve 150 not stick to or abrade the wound surfaces 2203, yet allow some fluid flow to the device 10.

Contaminating substances can often be found on the interior surfaces 2203 of internal wounds 2201, such as dirt, threads, or clothing fragments. In addition to causing internal bleeding, internal wounds 2201 often generate tissue fragments, blood clots, and dead or dying tissue into the wound cavity 2205. It can be advantageous to clear such contaminants from the wound site 2201.

In some embodiments, the sleeve 150 can provide a surface to aid in the subsequent debridement of the wound, by presenting a surface on which cellular debris 2217, bone and tissue debris 2217, can attach, such as shown in FIGS. 5A-5C. For cleansing an internal wound surface of foreign objects, the sleeve or sheath 150 can include an adhesive material 159, for example on its outer surface 154, that attracts and captures foreign objects present on the internal wound surfaces, such as threads and clothing fragments, bullet fragments, metal particles, slivers, and the like.

As shown in FIG. 8B, the expanded articles 120 can exert compressive force, outward from the device 10, against the sleeve 150. This action can cause the sleeve 150 to be affirmatively pressed against any free-floating debris 2217 in the wound 2201. This action can cause the sleeve 150 to be affirmatively pressed against any debris 2217 associated with the internal surfaces of the wound cavity 2205. In such manners, various types of wound debris 22217 can come into contact with, and adhere to, the sleeve 150.

As shown in FIGS. 5B-5C, when the sheath 150 is later removed from the wound of a patient, the sheath 150 can remove the objects caught on the sheath material, thus helping to clean the wound 2201 of damaged tissues or foreign objects. In some embodiments, when the device 10 is withdrawn from the internal wound 2201, the sheath or sleeve 150 (to which the foreign objects 2217 are adhered) is also removed, thus helping to clear the foreign objects 2217 from the wound 2201.

To remove non-cellular components, materials such as polymeric membrane dressings composed of a hydrophilic polyurethane membrane matrix with a continuous semipermeable polyurethane film backing, For example, to attract metallic components, the adhesive material 159 can include magnets or magnetic materials.

To remove cellular components, materials such as hydrogel dressings, can be used. Also, enzymatic debridement agents, such as collagenase, can be used to digest tissue components.

Other materials, such as microfibers or hydrogel can also be incorporated as general-purpose adhesive materials 159 for removing wither type of wound contaminant.

When the sheath is later removed from the wound of a patient, the sheath can remove the objects caught on the sheath material, thus helping to clean the wound of damages tissues or foreign objects.

The sleeve 150 can have surfaces that are smooth, rough, or textured, rough, to make the sleeve easier to grip and to facilitate the removal of the sleeve 150 (and the device 10 contained within the sleeve 150) from the wound path.

Like other components of the device 10, the sleeve 150 can comprise one or more therapeutic agents 104, or can contain one or more therapeutic agents 104 in proximity to the device 10. For example, the sleeve material can be coated or impregnated with substances deemed useful in treating bleeding wounds, such as a coagulant compound.

The sleeve 150 can comprise a covering made of a non-stick material, preferably a non-stick covering with pores 157 or openings to accommodate fluid flow such as gauze or TELFA™ bandages or dressings. Any material commonly used for dressing wounds can be used, not limited to microfibers, hydrofibers, alginate, foam, semipermeable polyurethane films, sponges, woven and non-woven fibers, plastic, and latex. However, to allow an inflow of liquid from the wound, it is preferred that the sleeve 150 be made of a naturally porous material, or that pores 157 or openings or slits be introduced into the sleeve 150 material.

Optionally, the sheath 150 can contain one or tearing paths, preferably positioned to be substantially parallel to a longitudinal axis of the device 10. For example, such tearing paths can define long, thin pathways that are scored or etched onto an inner or outer surface 152, 154 of the sleeve 150, or can include sections of material that are thinner than neighboring sections. Such tearing paths can relieve pressure on the sleeve 150 when the absorbent liquid-expandable materials 118 expand, and cause the sleeve 150 to develop tears that are large enough to relieve such pressures, but small enough that the expanded absorbent articles 120 remain captured within the sleeve 150.

Such non-stick covering can create a barrier to keep absorbent materials from the device 10 from sticking to the wound 2201 when placed directly on the wound 2201, but allow liquid to contact absorbent liquid-expandable articles 118 present in the device 10. The pores 157 can allow blood or liquid to flow into exterior structures of the device 10 (e.g., liquid-soluble coating 124), or allow therapeutic agents 104 to be delivered from the device 10 to the wound site 2201 and wound surfaces.

The non-stick covering can also serve to keep the absorbent material contained in proximity with the device 10. This feature can keep the absorbent material intact, to facilitate the subsequent removal of the device 10 in its entirety, so that no pieces of the device 10 are left behind in the internal wound 2201.

In some embodiments, the inner or outer surfaces 152, 154 of the sleeve 150 include a material to which clotted blood, wound fragments, dirt, and/or other contaminants can adhere. Thus, when the sleeve 150 is removed from the cavity 2205 of the wound 2201, the outer surface 154 can remove the detritus from the cavity 2205 and out of the internal wound 2201. For example, a magnetic substance could coat the inner surface 154 of the sleeve 150 for adhering and retrieving metal fragments from the wound 2201, or the sleeve 150 itself can be impregnated with a therapeutic agent 104 to which tissue fragments can adhere. In some sleeved embodiments, the sleeve 150 can be removed from the wound site 2201, 2205 after the device has been engaged with the wound 2201; where the sleeve 150 is treated to engage contaminants, the removal of the sleeve 150 can also be used to clear blood clots, tissue fragments, dirt, clothing fragments, and the like from the interior 2205 of the wound 2201.

Embodiment 2

As shown in FIGS. 5-8, an alternative embodiment relates to a dressing device 10 for treating an internal wound that includes a handling member 26 connected to an elongated portion 52 having a profile with a wide end and a narrow end. The elongated portion 52 can have a profile that is tiered or terraced, having segments that decrease in width in distinct and stepwise stages.

The device 10 can include a handling member 26 by which an individual can grasp the device 10. This handling member 26 can provide a means for the individual to insert the device 10 into an internal wound 2201; it can provide a means for an individual to manipulate or guide the device 10; and it can provide a means for the individual to withdraw the device 10 from the internal wound 2201.

The handling member 26 can include a base portion 20. The base portion 20 can have a first side 22 facing the elongated portion 52, and a second side 36 opposite the first side 22. The second side 36 can be positioned to rest in a location proximate to a site where the internal wound 2201 meets an external surface of the wounded individual's body (e.g., entry wound 2207 or exit wound 2211). When the device 10 is secured, the second side 36 can protrude from the internal wound 2201, be flush with the external surface of the body, or be seated within the internal wound 2201.

A user can choose a device 10 so that, when inserted into the wound 2201, the base portion 20 protrudes from the wound site (FIG. 5A), or lies flush along the wound site (FIG. 9B), or is partially or completely engulfed or contained within the wound site 2201.

The second side 36 of the base portion 20 can include, an outer surface that is flat, dome-shapes, or a curved surface or a curved dome, for example. The second side 36 can be smooth, textured, rough, or contoured.

As shown in FIGS. 5-8, the first side 22 of the base portion 20 can be connected or joined to the elongated portion 52. The elongated portion 52 can have first and second opposing ends, one of the ends having a greater width or perimeter than the other opposing end - - - that is, a first wide end 54 and a second, narrow end 56. The first side 22 of the base portion 20 can be connected or joined to the first wide end 54 of the elongated portion 52.

The elongated portion 52 can be made of a plurality of cylinders, tubular sections, or tubes 50. The cylinders or tubes 50 can enclose a hollow portion 63 or can have solid interior portions.

Each cylinder or tube 50 can have opposing first and second ends 68, 69, with a sidewall 58 defining the cylindrical structure between the ends 68, 69. Each cylinder or tube 50 can have a cross-section that is substantially square, rectangular, or triangular in shape, when the cross-section is taken through a plane along a central longitudinal axis of the cylinder or tube 50. A cross-sectional view of a plane perpendicular to the central longitudinal axis can reveal a substantially square, rectangular, trapezoidal, or triangular shape, though other shapes are contemplated.

The individual cylinders 50 can have a different diameter, circumference, or perimeter than a neighboring cylinder 50. The length of each cylinder 50 can vary considerably. The cylinders 50 can be joined end-to-end, with the first end 68 of one cylinder 50 joining or connecting with the second end 69 of a neighboring cylinder 50, except for the tubes 50 on the proximal and distal ends of the series of cylinders 50. The cylinder 50 most proximal to the handling member 26 can have a first end 68 joined to the base portion 20, while the cylinder 50 most distal from the handling member 26 can have a second end 68 unattached to another cylinder 50.

In preferred versions, moving from the wide end 54 to the narrow end 56 of the elongated portion 52, each successive cylinder 50 can have a smaller diameter, circumference, or perimeter than the preceding cylinder 50. The series of cylinders 50 can have graduated circumferences. Viewed in profile or cross-section, each successive cylinder 50 can have a narrower diameter or perimeter than the preceding cylinder 50, each successive cylinder 50 narrowing or reducing in size in discrete steps. It is preferred that the device 10 have segments that decrease in size in discrete steps, to provide the device 10 that narrows in a stepwise fashion, rather than a smoothly-tapering fashion. As shown in FIG. 9A-9D for example, the elongated portion 52 can have a profile with a wide end 54 and successive step-wise decreases in diameters of the cylinders 50, providing a generally cone-shaped profile that narrows in a terraced or stepwise fashion.

It is believed that the rigid, stepwise decrease in diameter provides a shape such that the device 10 provides little or no resistance against the internal surfaces of the wound 2201 until it is fully seated in place. Once seated, such device 10 with such shape can provide downward (or inward) force, helping the device 10 to remain seated in the wound 2201.

In such embodiments, individual cylinders 50 can have square or rectangular profiles, with increasingly narrower cylinders stacked in succession, as one moves away from the handling member 26. In other embodiments, such as where the individual cylinders 50 have trapezoidal profiles, the elongated portion 52 can have a profile showing a stepwise decrease in diameter or perimeter or it can have a tapering profile. Although it is preferred that the overall profile of the elongated portion 52 be widest near the handling member 26 and narrowest at the opposite end (or narrowest at a tip portion 16 of the device 10), individual cylinders 50 can have a diameter, circumference, or perimeter that is larger than both of its immediate neighboring cylinder 50.

Each cylinder 50 can include a sidewall 58 having an exterior surface 60 facing outward opposite an interior portion 61 facing inward. Each sidewall 58 can comprise a hollow cavity 63. Each sidewall 58 can surround or encase a solid core portion; where the hollow cavity 63 is also present, the sidewall 58 can surround or encase the hollow cavity 63. The sidewalls 58 of neighboring cylinders 50 can be aligned with respect to each other to define a solid core member 57 that runs the length of part or all of the device 10. Such solid core member 57 can provide strength and stability to the device 10.

Such hollow cavity 63 can define a space in which a therapeutic agent 104 are stored, the hollow cavity 63 for encapsulating and containing the medical treatment is stored. The hollow cavity 63 can define a space that extends from one, top end 68 of the cylinder 50 to the other, opposite, bottom end 69 of the cylinder 50, defining a passageway 64 for another substance, such as a medical treatment, or gas, or liquid, to travel from one end 68 of the cylinder 50 to the other end of the cylinder 50, and to a neighboring cylinder 50.

Where there are a plurality of cylinders 50, each having a hollow cavity 63, the hollow cavities 63 of each cylinder 50 can align against each other to provide communication between neighboring cylinder 50. In some cases, all of the hollow cavities 63 can line up or align to define a passageway 64 travelling through part or all of a hollow interior portion 63 of the device 10, from a top end 54 of the plurality of cylinders 50 to the opposite bottom end 56 of the plurality of cylinders 50.

As described above, each cylinder 50 can include an absorbent, liquid-expandable article 118. Such liquid-expandable article 118 can make up part of the sidewall 58 of each cylinder 50; such liquid-expandable article 118 can be located in the hollow portion 63 of the cylinder 50. Each sidewall 58 can provide an annular ring or continuous band of absorbent material surrounding a hollow portion 63 or surrounding a solid core portion of the cylinder 50. In some embodiments, the cylinder 50 can comprise a solid cross-section of one or more absorbent, liquid-expandable articles 118 running continuously throughout the cylinder 50.

The cylinders 50 can share a common central longitudinal axis, providing a device 10 with a symmetrical profile that can be described as linear or defining a straight line. In other embodiments, neighboring cylinders 50 can be joined at transverse angles to each other, to provide a device that defines a curved or arcing path, or defines an angular path, as seen in the cross-sectional views of FIGS. 3-4. Thus, different embodiments of the device 10 can be used to treat wounds having straight, curved, or irregular pathways.

Figures 9A, 9B:
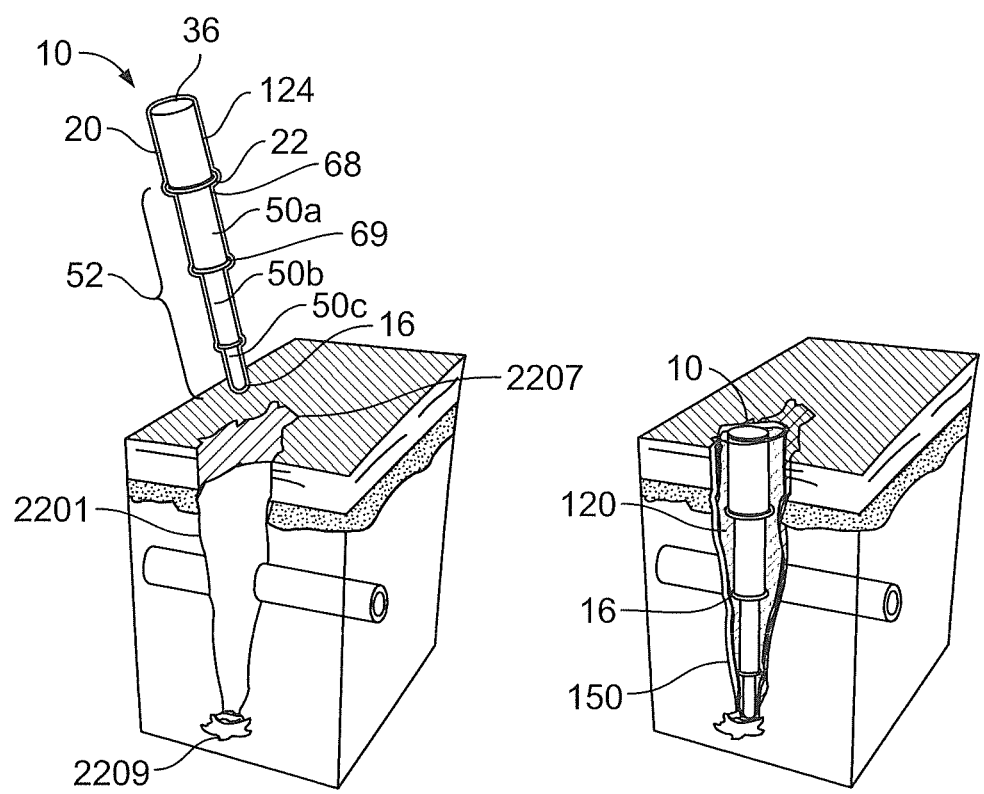
FIGS. 9A-9D illustrate therapeutic features of the temporary dressing.

The device 10 can include a layer or coating 124 surrounding a portion of or all of the exterior surfaces (e.g., 60) of the device 10 (FIGS. 4A and 9A). Preferably, the coating 124 surrounds or encases the plurality of cylinders 50 and can also encase the exterior surfaces of the base portion 20. Such coating 124 can provide a physical barrier around the absorbent, liquid-expandable article 118, to keep the absorbent, liquid-expandable article 118 in a moisture-free and unexpanded state. The coating 124 can include a liquid-soluble material, so that when the device 10 is deployed into a wound 2201 and the device 10 comes into contact with a liquid, such as blood or serum, the liquid-soluble coating 124 can dissolve or erode to expose the absorbent, liquid-expandable articles 118 of the device 10 the liquid. In turn, the liquid can then be absorbed by the absorbent, liquid-expandable article 118, converting the liquid-expandable article 118 into an expanded article 120. The expanded article 120 can swell and expand away from the device 10 and toward the interior surfaces 2203 of the wound 2201.

In some embodiments, the sidewalls 58 and hollow interior portions or cavities 63 can include therapeutic agents 104 for delivery to the wound site 2201, particularly coagulant substances, such as shown in FIGS. 6A-6B. Some embodiments can include an optional sleeve or sheath 150, such as FIGS. 5 and 8.

As shown in FIGS. 5A-5C, a sleeve 150 can be attached to the handling member 26, and can encase the elongated portion 52, such that upon engaging of the handling member 26 to remove of the device 10 from the internal wound 2201, the narrow end of the handling member 26 is withdrawn from the cavity 2205 of the internal wound 2201, and the central portion 155 of the sleeve 150 withdraws the outer or peripheral portion 153 of the sleeve 150 away from the internal wound 2201. Ideally, any debris 2217 piece adhered to an adherent material contained within the sleeve 150 remains adhered to the adherent material of the sleeve 150, and is removed from the wound 2201.

Additional Features

When the wound plug device 10 is seated in an individual, a health care provider might not be able to see where the device is located within the individual. A standard x-ray device could be used to determine the location of such device 10 within the wound site 2207. Such information could inform a health care provider about the size, length, and internal location of the wound path 2207, information that may not be ascertainable by mere visual inspection.

In some embodiments, the plurality of tubes, tubular sections, or cylinders 50 can incorporate a tracking element to aid in determining the position of the wound plug device 10 within the wound 2201 by x-rays, CT scans, sonogram, magnetic resonance scanning (MRI), or other similar medical detection method. The tubes 50 can include a structure or material easily detected by x-ray or other detection method; in some embodiments, the tubes 50 can be made of a material detectable by x-ray, such as shown in FIGS. 2A-2F.

For example, an external flange 82, internal retaining rim, second mouth 91, or exterior surface 60 of sidewall 58 can contain a detection material 97 detectable by e-ray irradiation. For example, each external flange 82 could comprise an annular ring of detection material 97 on the upper or lower surfaces of outer edge of the external flange 82. In some embodiments, each sidewall 86 could include a stripe, dot, or other shape of detection material 97 on an exterior or interior surface 60, 61.

When an individual has a wound plug device 10 seated within an internal wound 2201, and the internal wound site is x-rayed, a plurality of detection devices 97 can provide a three-dimensional roadmap that shows, for example, the location of each external flange 82 within the individual. By extension, this would provide a three-dimensional roadmap of the internal wound 2201 in which the device 10 is located.

In some embodiments, the detection material 97 can be provided in fewer than all of the tubes 50, e.g., in alternating tubes 50. In some embodiments, the tracking element can be limited to the distal-most tube 50 (or tube 50 furthest from the base portion 20), or to the narrow end 56 of the elongated portion 52. The detection material 97 can be made of x-ray detectable plastic or metal, or could include a bead or pellet made of an x-ray detectable material.

Such information could affect a health care provider's decisions in treating the patient and could facilitate the efficient removal of the wound plug device 10.

The devices 10 can be made in a variety of sizes, to accommodate different kinds of wounds (e.g., stab wounds versus bullet wounds), or to accommodate wounds of different sizes, such as shown in FIGS. 4-8. The device 10 can be manufactured in dimensions and lengths meant to accommodate wounds of different sizes, dimensions, depths, and configurations. For example, the device 10 can have dimensions suitable for treating a wound 2201 created by a firearm, such as shown in FIGS. 3-5.

The plurality of tubes 50 can be made in variety of lengths and circumferences (or diameters). While the tube 50 closest to the base portion 20 can be the largest of the tubes 50 and the tube 50 furthest from the base portion 20 can be the smallest of the tubes, the tubes can have diameters that range between 0.10 to 12 inches, 0.5 to 6 inches, or between 1 and 1 to 4 inches.

Where typical wound paths are known for certain types of firearm wounds, the device 10 can be manufactured to fit within such a wound path.

In addition, for specific kinds of injuries, devices 10 of specific size or configuration can be made. For example, as shown in FIGS. 6A-6B, devices 10 used for treating nose bleeds, or for stanching the flow of blood or fluid from the nasal cavities 2219 of a human being, the device 10 can have a profile that is preferably less than 3 inches in length, or less than 2 inches in length, or less than 1 inch in length. The plurality of tubes 50 preferably has diameters less than 2 inches, less than 1 inch, less than 0.5 inch, or less than 0.25 inches.

Figure 7:
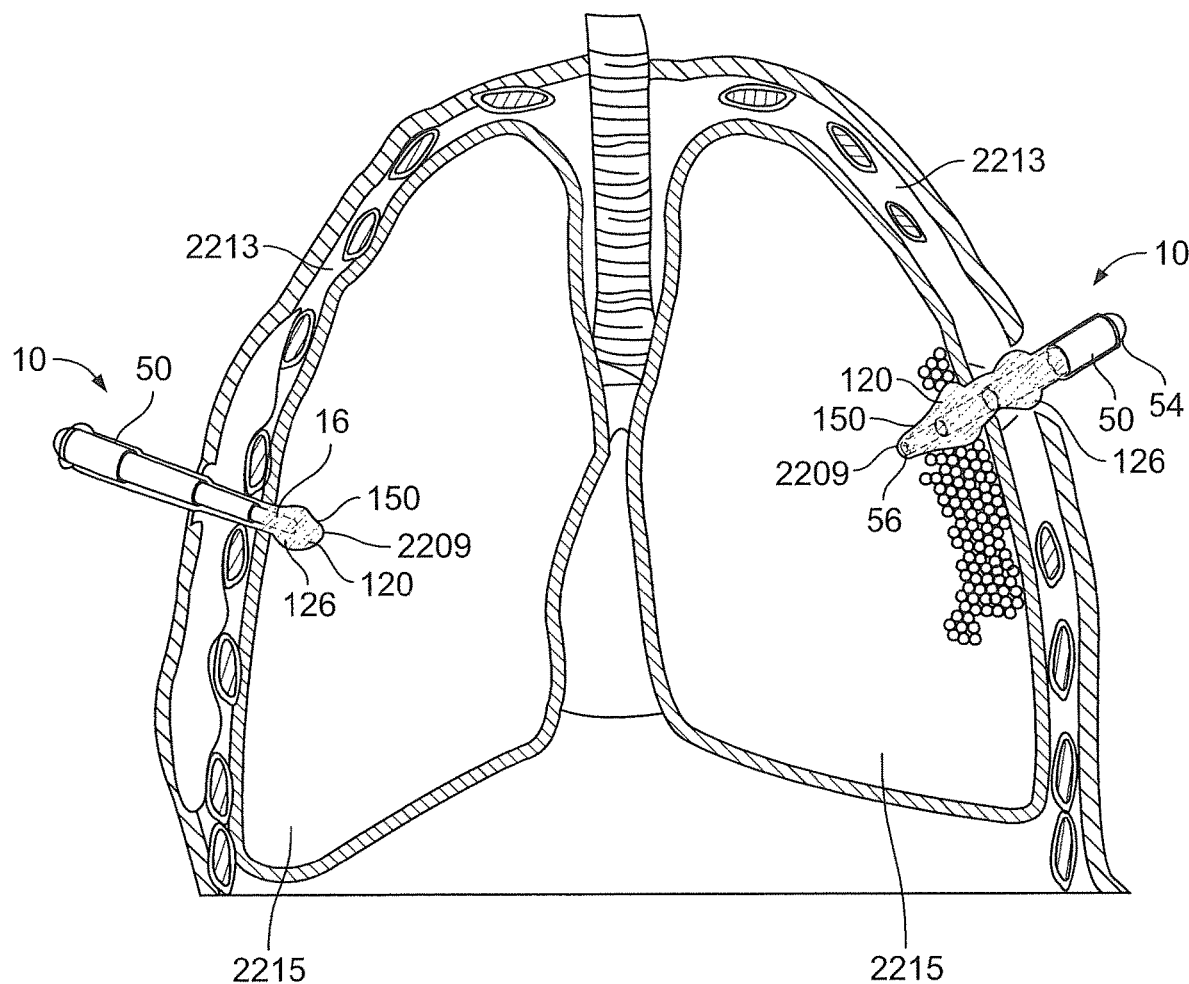
FIG. 7 shows a temporary dressing used to treat a hemothorax injury and a pneumothorax injury involving the lungs of an individual. Here, the dressings can provide a conformation that enable them to act as plugs that can close the internal wounds and can anchor the dressings in place.

As shown in FIG. 7, devices can be configured to treat hemothorax or pneumothorax injuries to the lungs or pleural cavity. With wounds extending into the lungs, a device 10 can be inserted into the wound 2201, and the associated liquid-expandable article 118 can absorb in situ liquids and become an expanded article 120.

An expanded article 120 inside proximate to the torso 2213 can expand to fill the wound cavity 2205 within the torso 2213. In some embodiments, the expanded article 120 can provide a sealing engagement with the torso 2213. The expanded articles 120 can expand to fill the void or space created by the wound cavity 2213 and the device 10 can thus conform to the regularly- and irregularly-shaped spaces within the wound cavity 2213.

An expanded article 120 inside a lung 2215 can provide a plug 126 within the lung 2215, the plug 126 comprising one or more expanded articles 120 having a volume large enough to bock or seal the wound cavity 2205. Such a plug 126 can provide an air-tight seal that can prevent, for example, the outflow of air from the lung 2215 or the inflow of air or liquid into the lung 2215. The formation of such a plug 126 can also serve to keep the device 10 stably engaged within the wound 2201.

Figure 8A:
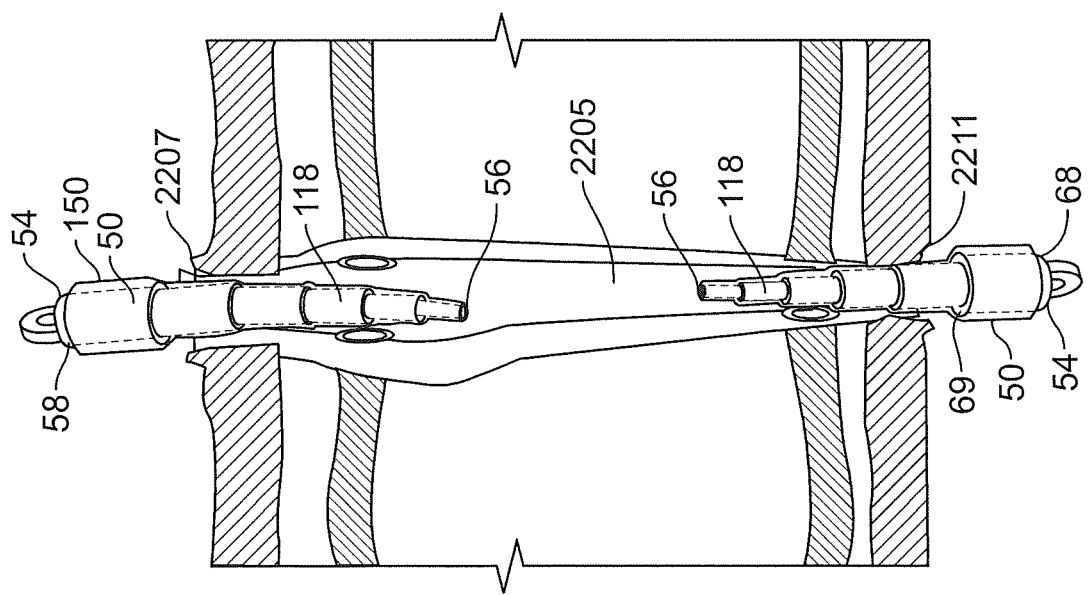

As shown in FIG. 8A-8B, devices 10 can be used to treat a through-and-through injury to a limb, such as an arm or leg, or a through-and-through injury to another portion of the body, such as a shoulder or torso 2213. After the devices 10 are inserted, pressure tape or other bandages can be used to secure the device 10 to the wound site 2201. When such bandage is used to wrap or compress the wound site 2201, it can deliver additional force toward a terminus 2209 of the wound 2201. Where the expanded articles 120 can provide a force directed outward from the device 10, that force can be mainly directed in directions radiating away from a central longitudinal axis of the device 10. In contrast, the wrapped device 10 can direct pressure in the same general direction of the central longitudinal axis of the device 10, delivering force in another direction or vector than the expanded articles 120.

In situations where the wound 2201 is particularly large, or where the size of the wound cavity exceeds the volume treated by a particular device 10, it can be desirable to insert more than one device 10 into the wound 2201. In the particular case of an injury having both entry and exit wounds 2207, 2211, it can be desirable to insert a device 10 into each site, so that the pair of devices 10 meet at a point somewhere in the interior 2205 of the wound 2201, such as shown in FIGS. 8A-8B.

The device 10 can include one or more therapeutic agents 104, as shown for example in FIGS. 6A-6B. Individual components, such as the base portion 20, tubes or graduated cylinders 50, or liquid-expandable article 118 can be impregnated or coated with one or more therapeutic agents 104. The plurality of tubes 50 or the elongated portion 52 can comprise a therapeutic agent 104. Individual components can be suffused with one or more therapeutic agents 104. Individual components, particularly one or more tubes 50, can include an interior compartment 100 containing one or more therapeutic agents 104 to be dispersed while the device 10 is applied to a wound 2201.

The therapeutic agents 104 can be chosen from the following group: analgesics, anesthetics, antibiotics, antiseptics, antibiotics, adhesives, anti-adhesives, coagulants, steroids, antihistamines, bactericides, disinfectants, fungicides, vasoconstrictors, chemotherapeutic drugs, keratolytics, cauterizing agents, antiviral drugs, epidermal growth factor, fibroblast growth factors, transforming growth factors, glycoproteins, fibrinogen, fibrin, humectants, preservatives, lymphokines, cytokines, odor controlling materials, vitamins, and clotting factors.

The therapeutic agents 104 can be a hemostatic agent; that is, an agent that stops bleeding or hemorrhage. For example, the one or more therapeutic agents 104 can include chitosan or a derivative of chitosan, kaolin, diatomaceous earth, silica, clays, minerals, attapulgite, bentonite, zeolite, and bioactive glasses.

The therapeutic agents 104 can include an inorganic salt, such as a divalent ion selected from the group consisting of zinc, copper, magnesium, calcium, nickel, CaO, $CaCl_2$, $AgNO_3$, $Ca(NO_3)_2$, $Mg(NO_3)_2$, $Zn(NO3)_2$, $NH_4NO_3$, AgCl, $Ag_2O$, zinc acetate, magnesium acetate, calcium citrate, zinc citrate, magnesium citrate, magnesium chloride, magnesium bromide, zinc chloride, zinc bromide, calcium bromide, calcium acetate and calcium phosphate.

The therapeutic agents 104 can be located at the base portion 20, the tubes 50 or the tip portion 16 (portion of the tubes 50 furthest from the base portion 20). Each element can comprise a therapeutic element 104. For example, the base portion 20, tube 50, or tip portion 16 can contain a therapeutic agent 104 coated on its surface, stored in an internal compartment 100, or incorporated within the structure itself.

Inserting and Removing the Device

The medical device 10 can be a portable apparatus that can be readily transported to an injured individual needing treatment for a bleeding internal wound 2201.

Here, insertion and removal of the device 10 will generally be discussed in terms of its application to the entry site 2207 of the wound 2201. However, where the wound 2201 also includes an exit site 2221, the device 10 can be deployed in much the same fashion with respect to the exit site 2221 as it can be deployed with respect to the entry site 2207.

As shown for example in FIGS. 4, 8, and 9, to apply the device 10 to an internal wound 2201, an individual can grasp the device 10 at the base portion 20 of the handling member 26, and position the device 10, so that the opposite end of the device 10 is positioned at the entry or exit site 2207, 2211 of the wound 2201, where the wound 2201 meets the exterior surface of the subject's body. In some embodiments, the distal-most tube 50 (or tube 50 furthest from the base portion 20 or furthest from the handling member 26) can be positioned at the wound site 2201. In some embodiments, a portion of the plurality of tubes 50 including the distal-most tube 50 (e.g., a tip portion 16) can be positioned at the wound site 2201.

In some embodiments, the narrow end 56 of the elongated portion 52 can be positioned at the wound site 2201, such as shown in FIG. 4A.

The tip portion 16 can include the narrow end 56 of the elongated portion 52. As shown in FIGS. 4A, 6A, and 9A, the tip portion 16 can provide a structure with a very small footprint—smaller than the wide end 54 of the elongate portion 52—to facilitate easy insertion of the device 10 into the wound 2201. The tip portion 16 can be sized small enough to fit within a typical entry wound 2207. Preferably, the tip portion 16 is sized small enough for easy insertion into the entry wound 2207 and into a portion of the wound path 2201 proximate to the entry wound 2207.

In some embodiments, the device 10 can have a length and width so much smaller than the length and width of the wound path 2201, the device 10 can be inserted into the wound 2201 with minimal or no direct engagement of the internal surfaces of the wound 2201.

It is envisioned that the tubes or cylinders 50 have circumferences or perimeters narrow enough to fit within a typical wound cavity 2205. Before the expanded articles 120 are deployed within the wound 2201, the elongated configuration of the device 10 makes it easy to insert into a wound cavity 2205 having a width greater than the width of the device 10. It is expected that the relatively narrow device, and particularly its narrowest point at the tip portion 16, will be easy to insert into a relatively larger entry wound 2207 and wound cavity 2205.

The individual can push or guide the tip portion 16 of the device 10 into the subject's wound 2201, with the gradually broadening profile of the device 10 facilitating subsequent insertion of neighboring, increasingly-wider cylinders, and possible enabling the insertion of the base portion 20 into the wound pathway 2201. As the device 10 is pushed deeper into the wound 2201, successive cylinders 50 with progressively larger diameters or perimeters are introduced into the wound 2201. The leading, thinner or narrower cylinders 50 can ease the way for the progressively thicker cylinders that follow them into the wound cavity 2205, which can facilitate the insertion of the tip portion 16 into the distal or deeper portions of the wound cavity 2205.

Thus, a device 10 with a base portion 20 that is wider than the tip portion 16 can be introduced into the wound site 2201, and the progressively larger widths of the series of cylinders 50 can be threaded or manipulated into the wound cavity 2205 with minimum resistance.

The generally elongated profile provided by the plurality of tubes 50 can minimize the engagement of the plurality of tubes 50 with an internal structure of the subject until the device 10 encounters the terminus 2209 of the wound 2201 (FIGS. 3A-3B), the device 10 is fully extended within the wound 2201 (FIGS. 7-8), or the device passes through the exit site 2211 of the wound 2201.

The elongated profile or cross-section of the device 10 can provide a device with a relatively narrower end whose shape and relative narrowness or thinness make the tip of the device 10 much smaller than the entry site 2207, and can facilitate the insertion of the device 10 into the entry site 2207 of the wound 2201. Because a terminal end of an internal wound 2201 can have a radius or circumference smaller than that of the entry site 2207, the wound cavity 2205 can have a profile that is wider near the entry wound 2207 and narrower near the exit wound 2211 (or narrower at the terminus 2209 of the wound 2201). In such wounds 2201, it is expected that such similarities in overall shape would facilitate the insertion of the device 10 deeper into the wound 2201, and that an individual would encounter less resistance in inserting the device 10, compared to a device with a non-elongated shape.

In embodiments including a plurality of pivotably-moving tubes 50 (e.g., Embodiment 1), neighboring pivoting tubes 50 can change position with each other, such as shown in FIGS. 3A-3B. For each pair of pivotable tubes 50, the pair of tubes 50 can adopt an angle that conforms to the portion of the wound path 2201 that the tubes 50 contact. As the device 10 moves through the wound cavity 2205 or wound path 2201, each pair of pivotable tubes 50 can adopt whichever angle will allow the tubes 50 to conform to the portion of the wound path 2201 that they contact, as the device 10 is inserted into or removed from the wound 2201.

For example, in a first portion of the wound path 2201, the pair of tubes 50 can adopt a first angle with respect to each other to conform to the first portion of the wound path 2201. As the device 10 moves from the first portion of the wound path 2201 to a second portion of the wound path 2201, the pair of tubes 50 can adopt a second angle with respect to each other to conform to the second portion of the wound path 2201. As the device 10 moves through the different portions of the wound path (e.g., third, fourth, fifth portions) 2201, the pair of pivotable tubes 50 can adopt whichever angle (e.g., third, fourth, fifth angles) that will allow the pair of tubes 50 to conform to that portion of the wound path 2201 that the tubes 50 contact. When the device 10 reaches a terminal end of the wound path 2201 (or extends as far as the length of the device 10 allows), the pair of tubes 50 can adopt a third (or final) angle with respect to each other to conform to the second portion of the wound path 2201.

In embodiments including a rigid or unmoving plurality of cylinders 50, (e.g., Embodiment 2), one or more devices 10 can be pushed into a wound site 2201, such as shown in FIGS. 8-9.

A particular advantage of the device 10 is that it can reduce or stop blood flow by more than one method, as shown by FIG. 9A-9D.

Several features of embodiments of the temporary dressing provide a device 10 that can be easily inserted into a wound 2201, which itself can define a pathway that cannot be determined by mere visual inspection.

FIG. 9A shows that the overall shape of the device 10 can mimic the general shape of a wound path 2201, providing a general shape for communicating with the wound path 2201. The tip portion 16 can include a tube or cylinder 50 having a width that is smaller than the opening provided by the entry wound 2207. Where the tip portion 16 is so much smaller than the entry wound 2205, the tip portion 16 is small enough to easily be inserted into the entry wound 2205 and proximal portion of the wound cavity 2205. The relatively small size of the tip portion 16 also can enable the device 10 to be threaded through the wound cavity 2205 to a wound terminus 2209 or out the exit wound 2211.

The device 10 has a compact shape. Its rigid structure, coupled with the stepwise decrease in volume from wider base portion 20 to narrower tip portion 16 provides a shape that generates little or no resistance against the internal surfaces of the wound 2201 as the device 10 travels through the wound path 2201. However, once the device reaches the terminus 2209 of a wound 2201 and fills that physical defect, the shape of the device 10 will provide a downward or inward force for keeping the device 10 in its place. Thus, the shape of the device 10 lends to ease of insertion into the wound 2201 and can promote the retention of the device 10 within the wound 2201, independent of other factors discussed herein.

Once inserted into a wound 2201, the device 10 can apply simple compression against the inner surface 2203 of the wound 2201, such as shown by FIGS. 3B, 8B, and 9B.

As shown in FIG. 9B, when the device 10 is seated within the wound 2201, liquid-expandable articles 118 can absorb liquid and expand in size to become an expanded article 120. When the expanded articles 120 have expanded sufficiently to contact the internal surfaces of the wound cavity 2205, the device can adopt a shape that allows it to communicate with the interior surfaces of the wound 2201, providing a form-fitting plug to close or seal the physical defect or cavity or hole provided by the wound 2201.

The expanded articles 120 can apply outward or sideward pressure against the exposed surfaces of the internal wound cavity outward or sideward pressure against the exposed surfaces of the internal wound cavity 2205. The expanded articles 120 can exert compressive force directly against the surfaces of the wound cavity, such as shown in FIG. 4B. The expanded articles 120 can exert compressive force indirectly against the surfaces of the wound cavity 2205 by pressing against a sleeve 150 encasing the device 10, pressing the outer surface 154 of the sleeve 150.

If a deployed device 10 is bound in place, or if manual pressure is applied to the base portion 20 of the device 10, additional downward pressure can be applied against the wound 2201. As such, compressive force can be applied against individual arteries, veins, and capillaries to minimize blood flow from such compromised fluid-transporting vessels. Moreover, the device 10 can be similarly deployed against biological structures other than circulatory vessels or vasculature. The device 10 be used to minimize fluid flow from other fluid-transporting biological structures that could intersect with a wound cavity 2205, such as lymphatic vessels, glands, ducts, and the like.

Figures 9C, 9D:
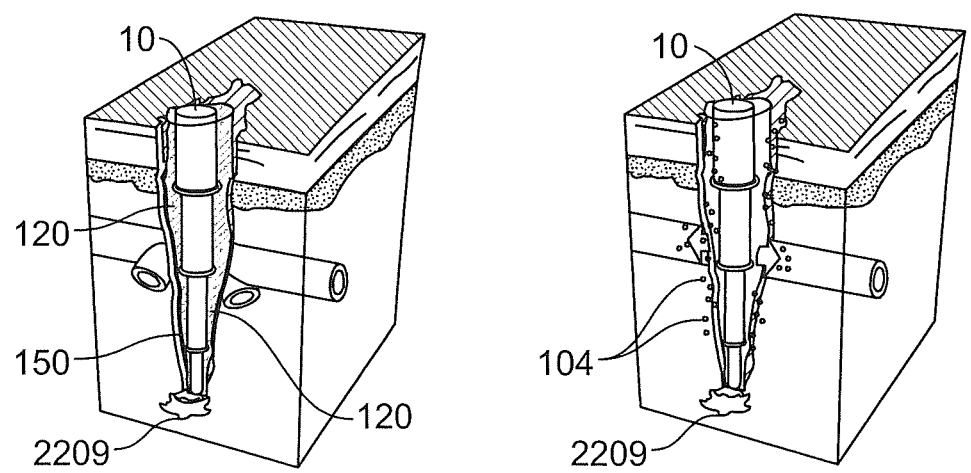

The the elongated, stepwise shape of the temporary dressing 10 can result in downward pressure applied to the wound 2201, such as as shown in FIG. 9B. In such situations, the device 10 can act as a self-plugging device. Where the elongated profile of the device includes cylinders or tubes 50 having increasingly smaller diameters or circumferences, a cross-section or profile of the device 10 can include a profile or cross-section decreases in width in a stepwise fashion. Such stepwise or terraced configurations can provide a device 10 that resembles a dowel. Like a dowel, such device 10 can be inserted into a narrow passageway and can seal or plug itself into the defect. In such situations, with a dowel-like device 10 mated to a long and narrow passageway, preferably of similar size, can exercise a self-plugging effect on the wound 2201.

Where a blood vessel is severed, and an end of the blood vessel communicates with the wound cavity 2205, the insertion of the device 10 can cause the blood vessel to fold over, such as shown in FIG. 9C. When fluids in the wound 2201 cause the liquid-expandable article 118 to enlarge and swell in the expanded article 120, the expanded article 120 can provide pressure on the folded blood vessel, thus crimping the blood vessel partially or wholly shut.

In addition to applying mechanical treatments to the wound 2201, the device 10 can also deliver chemical- or compound-based treatments to the wound 2201. The device 10 can include one or more therapeutic agents 104 that can be transferred from a portion of the device 10 into the wound site 2201, such as shown in FIG. 9D. Some embodiments include a therapeutic agent 104 incorporated within or onto the device 10. When the device 10 engages the wound 2201, the therapeutic agent 104 can be delivered to the wound 2201, and can provide a component also capable of reducing or stopping blood flow by chemical or biological means, such as shown in FIG. 9D. The device can dispense other types of therapeutic agents 104, such as a coagulant compound, into the wound site 2201.

When the tubes 50 reaches a terminus 2209 or inner surface 2203 of the wound 2201, the tubes 50 can provide compressive force against bleeding or seeping inner surfaces 2203, to reduce or stop blood flow from those inner surfaces 2203, as shown in FIGS. 3B and 9D.

The tubes 50 becomes saturated with liquid (i.e., blood), each liquid-expandable article 118 can absorb liquid present within the wound, causing the liquid-expandable article 118 to enlarge and swell in the expanded article 120. The expanded article 120 can partially or completely expands in volume to partially or completely fill the internal wound 2201. If it expands to a sufficient degree, the expanded article 120 can conform to the dimensions of the defect 2205 created by the wound 2201, such as shown in FIGS. 4A-4B.

The expanded article 120 can form a cavity- or crevice-filling mass for filling the defect 2205 defined by the wound path. The expanded article 120 can encourage a slowing or stopping of blood loss by, for example, compression against the internal wound site 2203, providing structures or surfaces to promote coagulation, or delivering therapeutic agents 104 to promote hemostasis. In effect, the expanded article 120 can act as a tourniquet, applying compressive force against the inner surfaces 2203 of the wound 2201. But instead of applying compressive force from the outside of the wound 2201, the device 10 can apply outward compressive force from the interior (or cavity 2205) of the wound 2201.

In some embodiments, the device 10 can be left in place. In others, it can be removed at a later time by grasping the base portion 20 and pulling the device 10 free.

In some embodiments, the inserted device 10 can be subjected to x-ray irradiation, or other detection methods, in order to reveal the placement of the device 10 within the internal wound 2201.

The device 10 can be inserted, guided, and removed by manual manipulation of the base portion 20. To remove the device 10, the base portion 20 can be grasped and pulled from the wound 2201.

In situations where a wound 2201 has both an entrance 2207 and an exit wound 2211, it can be desirable to insert a device 10 into each end 2207, 2211 of the wound path.

Where an individual suffers more than one internal injury, different devices 10 of the same or different size can be used in different wounds. Alternatively, multiple devices 10 can be deployed within the same wound 2201, where a single device 10 is not large enough to stop the bleeding of the wound 2201.

Where a caregiver cannot determine the size and path of an internal wound 2201, the adjustability of the device 10 profile enables a caregiver to use any-sized device and adjust or supplement as needed. The availability of a plurality of devices 10 allows for the treatment of several wound types without needing to predetermine the size and/or shape of a single expandable article 118 required to promote hemostasis.

In situations of mass casualties, where there are multiple injured individuals that require contemporaneous treatment, same-sized or different-sized devices 10 can be deployed to suit the nature of each individual injury. The dressings 10 can be applied by caregivers or by the wounded individual.

In situations where multiple injuries or multiple victims contemporaneously require immediate treatment for firearm injuries, punctures, or other internal wounds, there can be a need for multiple wound dressings 10 that can be distributed rapidly. In some embodiments, the medical device 10 can be included in a kit, which would typically include the medical device 10 and instructions, such as a product insert or label, instructing a use how to administer the device 10. In some embodiments, a kit could include a plurality of devices 10, of the same or different size; such kit could be desirable for situations of multiple wounds, multiple wounded individuals, or to accommodate a wide variety of injuries.

Specific embodiments of a temporary dressing 10 for an internal wound 2201 according to the present invention have been described for the purpose of illustrating the manner in which the invention can be made and used. It should be understood that the implementation of other variations and modifications of this invention and its different aspects will be apparent to one skilled in the art, and that this invention is not limited by the specific embodiments described. Features described in one embodiment can be implemented in other embodiments. It is understood to encompass the present invention and any and all modifications, variations, or equivalents that fall within the spirit and scope of the basic underlying principles disclosed and claimed herein.

What is claimed is:

1. A device for insertion into a wound path, the device comprising:

a handling member for handling the device, the handling member attached to one of a plurality of connected tubular sections;

the plurality of connected tubular sections, each tubular section comprising: a sidewall surrounding an interior portion, each sidewall including:
  first and second opposing ends defining first and second mouths, respectively; and
  a liquid-expandable article that swells into an expanded article upon contact with a liquid;
  an external flange extending outward from the first mouth, the sidewall defining a periphery of the first mouth; and
  an internal rim extending inward from the second end, the internal rim defining a periphery of the second mouth; and a liquid-soluble layer coating the plurality of connected tubular sections;

the plurality of connected tubular sections including a pair of neighboring tubular sections comprising proximal and distal tubular sections, the external flange of the distal tubular section located within the interior portion of the proximal tubular section, the external flange of the distal tubular section for engaging the internal rim of the proximal tubular section;

wherein, when the plurality of connected tubular sections are configured to be inserted into the wound path, the pair of neighboring tubular sections can move to adopt a shape conforming to a portion of the wound path; and wherein the device is configured to be disposed within the wound path such that the liquid-soluble layer is configured to dissolve upon contacting a liquid in the wound path, exposing each liquid-expandable article to the liquid; and each liquid-expandable article is configured to swell into the respective expanded article upon contacting the liquid in the wound path.

2. The device of claim 1:
wherein the neighboring tubular sections can form an angle between 0-15° in a horizontal plane; and
wherein the neighboring tubular sections can form an angle between 0-15° in a vertical plane.

3. The device of claim 1 wherein when the device is configured to be disposed within the wound path such that the expanded article provides a compressive force against an internal surface of the wound path.

4. The device of claim 1, comprising at least one therapeutic agent chosen from the following: an antiseptic, an antibiotic, an analgesic, an anesthetic, an adhesive, and a coagulant.

5. The device of claim 4 wherein each liquid-expandable article comprises the therapeutic agent.

6. The device of claim 1, wherein the device is configured to be disposed in a first portion of a wound path such that in the first portion of the wound path, the pair of neighboring connected tubular sections can adopt a first angle with respect to each other to conform to the first portion of the wound path;
wherein the device is configured to be disposed in a second portion of the wound path such that in the second portion of the wound path a second neighboring pair of tubular sections can adopt a second angle with respect to each other to conform to the second portion of the wound path; and
wherein the device is configured to be disposed in a third portion of the wound path such that in the third portion of the wound path a third neighboring pair of tubular sections can adopt a third angle with respect to each other to conform to the third portion of the wound path.

7. The device of claim 1, comprising a sheath encasing the plurality of connected tubular sections, the sheath comprising a stretchable material for containing each expanded article.

8. The device of claim 7, the sheath comprising a plurality of perforations.

9. The device of claim 1, the device comprising:
a tip portion, the tip portion comprising the distal tubular section disposed furthest from the handling member; and
a sheath surrounding the plurality of connected tubular sections, a central portion of the sheath attached to the tip portion, and the sheath comprising an adherent material, the adherent material for adhering to a piece of debris within the wound path;
wherein upon the removal of the device from the internal wound, the piece of debris is configured to remain adhered to the adherent material.

10. A kit comprising the device of claim 1.

* * * * *